United States Patent
Flendrig

(12)
(10) Patent No.: US 6,372,495 B1
(45) Date of Patent: *Apr. 16, 2002

(54) BIO-ARTIFICIAL ORGAN CONTAINING A MATRIX HAVING HOLLOW FIBERS FOR SUPPLYING GASEOUS OXYGEN

(75) Inventor: Leonardus Marcus Flendrig, Amsterdam-Buitenveldert (NL)

(73) Assignee: Seed Capital Investments-2 (SCI-2) B.V., Utrecht (NL)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/051,273
(22) PCT Filed: Oct. 4, 1996
(86) PCT No.: PCT/NL96/00389
    § 371 Date: Jun. 2, 1998
    § 102(e) Date: Jun. 2, 1998
(87) PCT Pub. No.: WO97/12960
    PCT Pub. Date: Apr. 10, 1997
(51) Int. Cl.⁷ .......................... C12N 11/02; C12N 5/00; C12N 5/08; C12M 1/00
(52) U.S. Cl. .................. 435/395; 435/177; 435/325; 435/370; 435/289.1
(58) Field of Search .................. 435/395, 398, 435/399, 400, 289.1, 370, 177, 325

(56) References Cited

U.S. PATENT DOCUMENTS

| | | | |
|---|---|---|---|
| 4,537,860 A | | 8/1985 | Tolbert et al. ............... 435/240 |
| 4,721,096 A | * | 1/1988 | Naughton et al. ........... 128/1 R |
| 5,262,320 A | | 11/1993 | Stephanopoulos et al. ...................... 435/240.23 |
| 5,510,262 A | | 4/1996 | Stephanopoulos et al. ...................... 435/240.23 |
| 5,549,674 A | * | 8/1996 | Humes et al. ................. 623/11 |
| 5,605,835 A | * | 2/1997 | Hu et al. ................. 435/297.2 |
| 5,622,857 A | * | 4/1997 | Goffe .......................... 435/378 |
| 5,686,289 A | * | 11/1997 | Humes et al. ........... 435/240.2 |
| 5,736,399 A | * | 4/1998 | Takezawa et al. ........... 435/399 |

FOREIGN PATENT DOCUMENTS

| | | |
|---|---|---|
| DE | 42 18 917 | 12/1993 |
| DE | 43 22 746 | 1/1995 |
| EP | 0 356 785 | 3/1990 |
| EP | 0 365 313 | 4/1990 |
| GB | 2178447 | * 2/1987 |
| WO | WO 94/16058 | 7/1994 |
| WO | WO 95/21911 | * 8/1995 |

OTHER PUBLICATIONS

Li, A.P. et al., In Vitro Cell Dev. Biol., vol. 29(A), p. 249–254, Mar. 1993.*
Bujia, J. et al., ORL, vol. 55(6), p. 347–351, 1993.*
Bhatia, S.N. et al., Annals of the N.Y. Acad. Sci., vol. 745, p. 187–209, 1994.*

* cited by examiner

Primary Examiner—David M. Naff
Assistant Examiner—Mike Meller
(74) Attorney, Agent, or Firm—Browdy and Neimark, P.L.L.C.

(57) ABSTRACT

A bio-artificial organ system is provided comprising a wall surrounding a space which has a solid support for cell cultivation. The space includes a there dimensional matrix in the form of a highly porous sheet or mat and including a physiologically acceptable network of fibers or an open-pore foam structure; hydrophobic hollow fibers permeable to gaseous oxygen or gaseous carbon dioxide evenly distributed through the three dimensional matrix material and arranged in parallel running from one end of the matrix material to the other end of the matrix material. Cells obtained from organs are present in the extra fiber space for culture wherein the cells are provided with sufficient oxygenation and are maintained as small aggregates with three dimensional attachment.

13 Claims, 6 Drawing Sheets

BIO-ARTIFICIAL ORGAN CONTAINING A MATRIX HAVING HOLLOW FIBERS FOR SUPPLYING GASEOUS OXYGEN

FIELD OF THE INVENTION

The present invention relates to the field of the cultivation of cells, especially of adherent tissue cells such as liver cells. More in particular, the invention relates to the field of biological methods and reactors for the cultivation and/or maintenance of cells, especially liver cells, and to the use of such methods in a bio-artificial liver system (BAL).

BRIEF DESCRIPTION OF THE PRIOR ART

It is generally known that most tissue cells require a solid support on which to grow and divide.

Although it is possible to culture adherent tissue cells in ordinary vessels, such as glass bottles or Petri dishes, during which the cells adhere to the wall of the vessel, usually special reaction vessels or bottles with a high surface area are used so as to provide increased capacity for cell attachment. One way to improve said surface area is to use a solid support for cell adherence. Such solid supports are known in the art; examples include glass beads, microcarriers and cellulose fibers.

A special problem in the cultivation of adherent cells—compared to the cultivation of cells in suspension or in confluent layers—is to provide sufficient nutrients and/or oxygen to the cells and/or provide for sufficient removal of waste products and/or carbon dioxide. This is especially a problem with cells that put stringent demands on both oxygenation as well as the removal of waste products, such as liver cells.

The non-availability of suitable solid supports and methods for the in vitro cultivation of liver cells has over the last 40 years severely hindered the development of the so-called bio-artificial liver (BAL) systems, systems that could be used in patients with liver defects for the support and/or replacement of the natural liver function.

As acute liver failure has a very poor prognosis and is usually fatal to the patient within days or even hours [see for instance Devlin et al., Hepatology Vol. 21, No. 4 (1995), pages 1018–1024 and Lake and Sussman, Hepatology, Vol. 21, No. 3 (1995), pages 879–882, describing the general problems in the art of the treatment of liver failure, both incorporated herein by reference], because livers for transplant are not readily available, a BAL system that could support and/or replace liver function, for instance during the time the patient awaits for a liver to become available for transplant and/or to bridge the period until the liver of the patient sufficiently recovers and/or regenerates by itself and/or as a result of treatment, would be highly desirable.

However, due to the abovementioned lack of suitable methods and/or materials for cultivating and/or maintaining liver cells in vitro, the bio-artificial liver systems from the prior art have so far proved insufficient, because they do not fully replace all the functions carried out by the liver of the patient in vivo, because they have insufficient capacity, and/or because the time during which they are therapeutically effective is too limited for practical use.

The history of bio-artificial liver systems has been described in a number of recent articles, notably Nyberg et al., the American Journal of Surgery, Vol. 166, November 1993, p. 512–521, and Sussman and Kelly, Scientific American, May-June 1995, p. 59–77, incorporated herein by reference.

As described in these articles, the earliest liver support systems were based on hemodialysis, charcoal hemoperfusion, or cross-hemodialysis either between humans or between humans and animals. Also, extra-corporeal liver perfusion has been tried.

All these systems have been found to be insufficient. As stated by Nyberg et al.:

based on the limited success achieved by early liver support techniques, the concept evolved that liver functions essential for survival would be best provided by mammalian liver preparations that allowed sustained or repetitive application. These liver preparations, commonly referred to as hybrid or bio-artificial systems, contain biological components within a synthetic framework. Biological components may include isolated liver enzymes, cellular components, slides of liver or cultured hepatocytes. Hepatocytes may be implanted in the patient or perfused extra-corporally. Hepatocytes systems have shown the greatest promise for bio-artificial liver support. When compared with cellular component and isolated enzyme systems, hepatocyte systems should supply a greater number of liver functions, since they utilize intact, metabolically active liver cells ( . . . ). One major advantage of the hepatocyte bio-artificial liver over traditional hepatocyte transplantation and earlier support techniques, such as cross-circulation and extra-corporal liver perfusion, is that the bio-artificial liver can be constructed from semipermeable materials that provide a barrier between the hepatocytes and the host immune system. As a result bio-artificial liver therapy may be performed without immunosuppression, and hepatocytes from different species (xenocytes) may be used within the bio-artificial liver.

The disadvantages of bio-artificial liver systems include ( . . . ) the problem of maintaining normal hepatocyte viability and function at the high cell density necessary for clinical application. For example, when hepatocytes are grown on a plastic surface with standard cell culture medium, they lose their gap junctions in about 12 to 24 hours; they also flatten and become a granular; tissue specific functions are lost in 3 to 5 days, followed by hepatocyte death within 1 to 2 weeks. As a result, improved techniques of cell culture have become necessary for the application of bio-artificial liver support systems.

A number of different approaches to the cultivation of hepatocytes and related cells for use in or as BAL-systems have been described. However, the prior art hepatocyte systems also suffer from problems with regard to capacity and effective working time, see Sussman and Kelly:

With regard to the provision of sufficient metabolic capacity, it is not clear exactly how much liver necrosis is fatal. Animal experiments suggest that at least 30% of the liver's original function must be preserved in order to survive. The adult human liver contains approximately 1000 gm of hepatocytes, which are the metabolically active cells. Thus we have proposed that effective liver assistance will require the equivalent of 300 to 400 gm of cells. Two sources of hepatocytes are available: freshly isolated cells (primary cultures) and cells grown in continuous culture (cloned or immortalized cells). Cells that have been isolated from a normal human or animal liver retain many of their functions ( . . . ) the technology has severe limitations.

Artificial livers that use freshly isolated cells have so far provided only a fraction of the necessary metabolic capacity. Hepatocytes do not divide after they have been isolated, so a steady supply of new cells is required. Coupled with the labour-intensive nature of cell preparation, this makes it almost impossible to scale up production to meet current needs in a cost-effective manner. Moreover, freshly isolated cells do not appear to last very long during treatment. A liver assist device that lasts for only 6 to 7 hours, as some have been reported to do, clearly falls short of allowing liver regeneration. Finally, production of any such device using animal cells entails a number of problems, especially in areas of sterility and lot-to-lot variability.

Uchino et al., ASIAO Transactions 1988;23;972–977 describe a hybrid bio-artificial liver composed of multiplated hepatocyte monolayers. A total of 80 grams of cultured adult dog hepatocytes was cultured in a reactor comprising a stack of 200 collagen coated borosilicated glass plates. These hepatocytes were viable and functioned well during 4 weeks in perfusion culture. This bio-artificial liver was tested in anhepatic dogs. The longest survival obtained was 65 hours.

However, a serious drawback of this system, besides the complexity of constructing and using a 200 glass plate-reactor, is that the monolayer culture of hepatocytes on said plates precludes the advantageous formation of hepatocyte aggregates. It is well known in the art that hepatocytes cultured in or as aggregates function both longer and better than hepatocytes cultured in monolayers, showing higher activity and better differentiation.

Another approach in the development of bio-artificial liver systems has been the use of hollow fiber bioreactors in which liver cells are present in the extra fiber (extraluminal) space while a liquid medium is pumped through the fiber lumen (intraluminal space), usually by perfusion with whole blood or plasma.

Rozga, Demetriou et al., Biotechnology and Bioengineering, Vol. 43 (1994), incorporated herein by reference, give an overview of the current hollow fiber systems. Their own system consists of a high flow plasma perfusion circuit comprising a charcoal column and a porous hollow fiber module with 5 to $6 \times 10^9$ microcarrier-attached porcine hepatocytes seeded into the extra fiber compartment. Because of the use of solid support (collagen coated dextran microcarriers), the surface area available for hepatocyte attachment is increased.

However, this design requires a separate membrane oxygenator for the oxygenation of the plasma to be incorporated into the perfusion circuit so as to provide sufficient oxygen to the hepatocytes in the hollow fiber module. Therefore, said oxygenation as well as the removal of carbon dioxide are dependent upon limiting factors such as the solubility of oxygen and carbon dioxide in the plasma and the transport of the oxygenated plasma throughout the reactor. Because of these limitations said hollow fiber reactor cannot easily be scaled up to a capacity required for practical therapeutic application.

Furthermore, this reactor is used with a very "closed path" column with a high density of the microcarriers, which leads to the formation of microcarrier pellets and to mass transfer problems with regard to the cells at the center of such a pellet.

Another disadvantage of this system is that the hepatocytes first have to be immobilized on the micro-carrier before the hepatocytes can be introduced into the hollow fiber reactor. This involves further complicating processing steps that can lead to loss of cell viability.

Sussman and Kelly, mentioned hereinabove, describe a hollow fiber-based bio-artificial liver system in which liver cells are attached to capillaries through which whole blood from the patient is pumped.

According to this system, the liver cells are oxygenated by the patient's blood, because—as stated by the authors— "plasma does not provide the oxygen carrying capacity of whole blood".

Furthermore, perfusion with whole blood can lead to the fibers and/or the pores thereof within the bioreactor getting clogged, which problem could only be solved by totally replacing the hollow fiber module, requiring a fresh isolation/immobilization of the hepatocytes.

Other disadvantages of this and other hollow fiber systems using whole blood as the liquid medium are that "the hollow fiber membrane must first act as a plasma separator before any significant transport of nutrients and metabolites can take place across the fiber wall", and that it "requires systemic anticoagulation with heparin to prevent clotting in the module".

Also, in order to overcome problems with the isolation of cells, in this BAL-system a special cell line named C3A derived from a liver tumor of a child is used. However, with regard to activity and function, the use of such tumor-derived cell lines is generally less preferred in the art than the use of isolated primary hepatocytes, also from a safety standpoint.

Furthermore, the C3A cell line used by Sussman lacks some very important functions of primary hepatocytes. Also, the C3A cells are less differentiated, and therefore less active than primary liver cells.

A somewhat different hollow fiber system is described by Nyberg et al., mentioned hereinabove; hepatocytes are suspended in a collagen gel, which is injected into the lumen of hollow fibers. After that, the extra fiber space of the bioreactor is perfused with medium for 24 hours, after which the gel contracts within the fibers, thereby creating a third space which is perfused with medium.

The idea behind this three-compartment design is that blood can be pressed through the extra fiber compartment, whereas the gel entrapped cells are nourished and possibly stimulated by the factors present in the medium flowing through a path adjacent to the contracted collagen.

However, this system also requires a complicated and time consuming pre-immobilization of the hepatocytes.

Another BAL-system based on capillaries for hepatocyte immobilization is described by Gerlach et al., Transplantation, Vol. 58, No. 9 (1994). Their bioreactor consists of a three dimensional framework for decentralized cell perfusion with low metabolite gradients and decentralized oxygenation and $CO_2$-removal, consisting of a woven network of four discrete capillary membrane systems, each serving different purposes, i.e., I, plasma inflow (polyamide fibers); II, oxygenation and carbon dioxide removal (hydrophobic polypropylene fibers or silicon fibers); III, plasma outflow (polysulfone fibers); and IV, sinusoidal endothelial co-culture (hydrophilic polypropylene fibers). These capillaries must be woven in such a way that the majority of hepatocytes find all four types of membranes in their surroundings.

This reactor was used with $2.5 \times 10^9$ pig hepatocytes with a viability between 88 and 96%, which were co-cultured with autologous sinusoidal endothelial cells present in the co-cultured compartment of the reactor.

In this type of hollow fiber bioreactor the liver cells have to be attached directly to the hollow fibers as no further matrix material for cell attachment is present in the reactor. In order to obtain sufficient attachment of the cells, the surfaces of the fibers must first be coated with a proteineous basement membrane product, such as Matrigel® or other collagen-based materials, requiring a separate and expensive pretreatment step. Even so, as hollow fibers are not specifically designed and/or suited for use as a solid support in cell cultivation, the attachment and the speed thereof permitted by and/or obtainable with said reactors is limited and heavy inoculum charges are required when seeding the reactor.

Furthermore, the average fiber distance within said three-dimensional fiber framework is about 500 μm, leading to the formation of large cell aggregates of comparable size. Again, these large aggregates can lead to mass transfer problems with regard to the cells in the center of said aggregate.

Also, it is well known that hollow fibers are difficult to process, and in this respect the manufacture of the very complicated three-dimensional fiber network described by Gerlach et al., comprising four separate discrete capillary systems, suffers from a disadvantage from an economical point of view. Also, this reactor is complicated to operate, requiring multiple separated inlet/outlet control systems.

A general problem of all the abovementioned hollow fiber bioreactors of the prior art is that the liquid medium (blood, plasma) to be treated is separated from the hepatocytes by the hollow fiber membrane; in other words, that there is no direct contact between the liquid medium and the hepatocytes in the reactor. Nutrients and substances to be removed from the liquid medium and/or to be secreted into the liquid medium, have to pass through said membrane barrier in order to reach the hepatocytes and the liquid medium, respectively. The passage through the membrane can lead to transport phenomena that can limit the achievable mass transfer, and therefore the efficiency of the BAL-system.

Also, the membranes can get clogged, especially when perfusion with whole blood is used. In that case the BAL system or parts thereof have to be replaced, which means that therapy has to be interrupted or even stopped.

Another important limiting factor in the membrane transport is the molecular weight cut off of the membrane, see Nyberg et al.:

Permeability and membrane molecular weight cut off influence waste removal, product delivery, and immune activation. Performance of biotransformation functions and the removal of nitrogenous wastes are important functions of the bio-artificial liver, along with the removal of red blood cell breakdown products such as bilirubin. The production of coagulation proteins and other serum proteins by hepatocytes in the bio-artificial liver may also be beneficial to patients with liver failure. However, these proteins are of comparable sizes to antibodies, which could have an adverse effect when directed against nonautologous hepatocytes in the bioreactor. Alternatively, small peptide products of the hepatocytes may exit the bioreactor and serve as antigenic stimulant in the patient. Whether these foreign molecules will result in harmful cytokine production, immune complex formation, or serum sickness in patients with liver failure remains to be determined. Potential side-effects must be addressed experimentally in order to determine the best molecular weight cut off for use in the bio-artificial liver.

Clinical treatment of hepatic failure requires large scale, high density hepatocyte culturing. In many bioreactors this gives rise to the formation of non-physiological hepatocyte pellets. Hepatocytes in the center of these large aggregates show poor metabolic activity and even possible necrosis due to high gradients as a result of hindered transport of nutrients and oxygen to and carbon dioxide, toxins and cell products from these cells. This is in contrast to the in vivo liver where every hepatocyte is in close contact with the blood. Besides, in most systems substrate exchange depends on diffusion which further limits mass transfer compared to the in vivo situation where hepatocytes function under perfusion conditions with low gradients.

Also, the bioreactors of the prior art are limited with respect to the amount of liquid medium that can be withdrawn from the hollow fiber lumen, as in general the fusion transport will be too slow. Therefore, an active withdrawal of liquid medium from within the hollow fibers will be required, even so, the total flow through the hollow fiber membrane will be very slow and/or lead to the undesired formation of gradients, even with a high flow of liquid medium through the hollow fibers themselves.

Another general problem with the bio-artificial liver systems of the prior art is that they require the use of liver cell preparations with a high viability (>80%) and a high attachment. As already acknowledged by Sussman and Kelly hereinabove, the production of such cells is a very costly, complex and time-consuming process requiring isolation and subsequent cultivation of suitable liver cells in sufficient viability and quantity which involves complicated procedures that do not reliably afford the required results, even when carried out by qualified experts.

Furthermore, known hepatocyte-containing BAL-systems cannot be stored before use for a prolonged period of time because the viability and function of the liver cells in the reactor cannot be maintained at a therapeutically acceptable level.

Also, the only technique available for preserving isolated liver cells over a longer period of time, i.e., cryopreservation, does not afford cells that are suitable for use with known BAL-systems, see Rozga et al., mentioned hereinabove:

availability of cells on demand becomes a very important consideration in the clinical setting where treatment of patients with FHF is carried out emergently, on short notice and at all hours. However, [cryopreservation] may result in a significant loss of cell viability [. . . ] and attachment (as much as 50%). [. . . ] Therefore, in clinical settings, we prefer the use of freshly isolated, well attached hepatocytes.

Because of these problems, the known BAL-systems cannot be used as "off the shelf" units that can be kept and/or maintained in hospitals until their use is required, as is the case with other artificial systems for organ support such as for instance dialysis machines or artificial heart or lung systems. Also, replacement during therapy of a spent primary liver cell based BAL system of the prior art with insufficient function with a fresh BAL system is usually not economically feasible over a prolonged period of time.

For instance, Demetriou reports that after 6 hours of use, 50% of the primary liver cells within his reactor die, whereas within 24 hours all cells have died. Better results have been obtained by using immortalized cells or the C3A cell line reported by Sussman et al., however, the use of this hepatoblast derived cell line has other disadvantages as already mentioned hereinabove.

In view of the above, there is a continuing need for bio-artificial liver systems that do not have the abovementioned disadvantages of the prior art systems.

The British patent application 2,178,447 describes a matrix for cell cultivation in vitro providing an increased available effective surface area for cell attachment provided by a fiber network or open-pore foam with a suitable pore size 10 μm to 100 μm. This matrix material can be provided in the form of a sheet or mat or in the form of particles or flakes, in which latter form it is marketed by Bibby Sterilin under the name Fibra-Cel®. As a sheet or mat, this matrix material has an appearance like filter paper or tissue paper, or thin porous felt.

This matrix material has some specific advantages over micro-capsules, which are costly and delicate to produce and give problems at high cell density growth, because frequently cells at the center of the capsule die. Also, the microcapsules may burst prematurely losing their contents and each new inoculation requires a fresh encapsulating procedure. Compared to microcarriers the matrix material according to GB-A-2,178,447 has the advantage that the cells are immobilized within the matrix structure. With microcarriers, these cells are immobilized on the outside of the carrier particles, making them susceptible to shear stress and particle collisions, for instance during preparation or packing of the reactor.

Furthermore, in the matrix material according to GB-A-2,178,447, the cells can proliferate along the fibers of the sheet in three dimensions (3D), rather than in two dimensions as in conventional tissue culture bottles, flasks or Petri dishes or on microcarrier beads or hollow fibers. Cells may attach themselves to more than one fiber and cell growth takes place in the internal volume of the fiber matrix. For these reasons, this and similar matrix materials are known in the art as "3D-carrier matrices".

Another advantage of said 3D-matrix material is that it does not require the heavy inoculum charges of two dimensional systems (20–30% of the final amount of cells at saturation), but can be inoculated at amounts of less than 10%, and as low as 5%. The three dimensional network provides for a higher—and quicker—"capture" of the cells, thereby also making it possible to use cells with sub-optimal attachment.

The GB-A-2,178,447 furthermore describes a number of potential bioreactor geometries employing the matrix material described therein. One of these comprises a sheet of said matrix material, rolled up into a spiral between two flattened tubes, wherein each alternate flattened tube serves a conduit, one for liquid nutrient medium, and the other for gases such as oxygen, air, $Co_2$ and water vapor.

However, GB-A-2,178,447 is not directed to the construction of bio-artificial liver systems, nor to the specific problems relating to the cultivation and/or maintenance of hepatocytes therein. In particular, GB-A-2,178,447 does not relate to the special problem of supplying sufficient oxygen to highly oxygen dependent hepatocytes.

In fact, the use of the "spiral wound" reactor according to GB-A-2,178,447 for culturing and/or maintaining hepatocytes would in practice lead to insufficient oxygenation, because the oxygen is supplied by means of just one conduit covering the entire length of the matrix mat. The use of such a single conduit would lead to the generation of an undesired oxygen gradient along its length or even to local oxygen depletion, especially when the reactor is scaled up by increasing the number of matrix windings.

Also, the bioreactor construction according to GB-A-2,178,447 contemplates a separate conduit for the supply and/or removal of the liquid medium, so that during use as a BAL, nutrients, toxins and other substances to be absorbed or secreted would have to pass through the membrane surrounding said conduit in order to reach the hepatocytes, giving the problems with regard to membrane transport and mass transfer as described hereinabove.

Furthermore, the use of a singular spiral wound conduit for liquid transport can lead to an inhomogeneous supply of liquid medium to all the parts of the bioreactor, for instance by the generation of undesired gradients.

All these factors make the matrix material as such and the bioreactor according to GB-A-2,178,447 unsuited for use in the cultivation of liver cells and/or for use as a BAL.

SUMMARY OF THE INVENTION

It is therefore a first object of the invention to provide an improved solid support and bioreactor for the cultivation and/or maintenance of adherent cells, especially liver cells, with improved cell adherence properties and improved supply and/or removal of gaseous components such as oxygen and carbon dioxide, even when used in or as a large scale bioreactor.

It is a further object of the invention to provide an improved solid support and bioreactor enabling direct liquid contact between the cells and the liquid medium to be treated while at the same time maintaining a homogeneous flow of liquid medium to all parts of said support.

It is another object of the invention to provide a method for the culturing of liver cells, with which liver cells can be kept viable in an amount and during a period of time that are practical for use in a bio-artificial liver.

A further objection of the invention is to provide a bio-artificial liver with improved therapeutic characteristics that can be used to replace and/or supplement the liver function of a patient.

Yet another object of the invention is to provide a method for the treatment of liver failure, especially acute liver failure, by using a bio-artificial liver.

Further objects of the invention will become clear from the description hereinbelow.

DETAILED DESCRIPTION OF THE INVENTION

Figure 1:
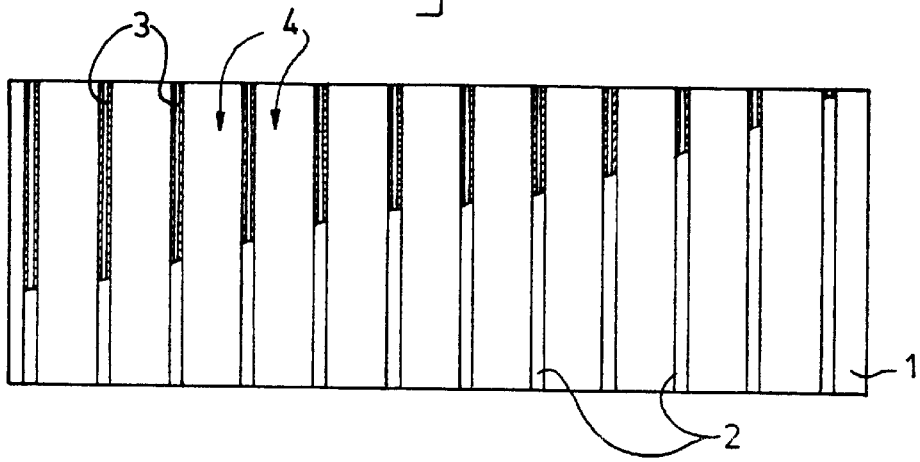
FIG. 1 shows a front view the preferred solid support of the invention.

It has now been found that an improved solid support for the cultivation of cells can be obtained by providing a 3D matrix material as described hereinabove, and in particular the matrix material according to GB-A-2,178,447, with hollow fibers for supplying and/or removing gaseous components such as oxygen and/or carbon dioxide, said solid support being especially suited for the cultivation of adherent tissue cells, such as human or animal liver cells.

It has also been found that an improved bio-artificial liver system can be provided using the solid support of the invention.

In general terms, the invention therefore relates to a solid support, comprising a 3D-matrix material and hollow fibers for gas transport;

a method for preparing said solid support, comprising attaching hollow fibers to a 3D-matrix material;

a biological reactor, comprising the solid support of the invention;

a method for the cultivation and/or maintenance of cells, especially adherent tissue cells, and in particular liver cells, using the solid support and/or the bioreactor of the invention;

a bio-artificial liver system, comprising the solid support and/or the bioreactor of the invention;

a method for replacing and/or supporting liver functions in a patient, and/or a method for the treatment of liver disorders, comprising the use of the bio-artificial liver system of the invention.

Further aspects, embodiments and advantages of the invention will be made clear by means of the description hereinbelow.

The Solid Support

The solid support of the invention in general comprises a 3D-matrix material and hollow fibers.

A 3D-matrix is defined herein as a material providing for a three dimensional for the growth of cells cultured therein. Such 3D-matrices are known to one skilled in the art; Examples are:

1. Gelfoam (gelatin, size: 20 mm*7 mm, Upjohn Ltd., Tokyo Japan).
2. PVF (collagen coated Reticulated Polyvinyl formal resin, size: 2 mm thick industrial filter material having a porosity of 80%, Kanebo Kasei Co., Osaka, Japan).
3. PVLA-RPU (poly-N-para-vinylbenzyl-lactonamide coated reticulated polyurethane, size: 34 mm diameter, 1 mm thick, Sanyo Chemical Industries, Ltd., Kyoto, Japan).
4. PGA (polyglycolic acid), Albany International Research Co., Mansfield, Mass.).
5. PVA (polyvinylalcohol), Unipoint Industries, Highpoint, N.C.).
6. PGA/PLA (polyglycolic acid/polylactic acid, ratio 90:10), Ethisorb).
7. 3D-Polyurethane foam or nonwoven matrix.
8. Porous silicon rubber foam (Ashby Scientific Ltd, Leicestershire, UK).

Preferably, said 3D-matrix is a material providing a high-surface area substrate, the effective surface of which is from 10 to about 100 times the area of the same projected onto a plane surface, comprising a physiologically acceptable network of fibers having a porosity from 40 to about 95% and a pore size of the order of 10 $\mu$m to 100 $\mu$m, or an open-pore foam structure with a pore size from about 10 $\mu$m to 100 $\mu$m, the overall height of the matrix being of the order of 50 $\mu$m to about 2000 $\mu$m, preferably 100–1000 $\mu$m, said matrix being in the form of a highly porous, nonwoven sheet or mat.

This material, as well as its preparation, its advantages and its preferred embodiments, are described in the British Patent application 2 178 447, mentioned hereinabove and incorporated herein by reference.

The matrix preferably has an open pore foamed polymer structure with pores from about 10 $\mu$m to 100 $\mu$m and a porosity of from 60 to 95%.

The matrix can be made from any suitable material mentioned in British Patent application 2 178 447, but is preferably made from a polyester.

The matrix material can also be used in any form as described in British Patent application 2 178 447, but is preferably used in the form of a nonwoven three dimensional fabric structure such as a sheet or mat; such flat, highly porous, non woven sheets or mats and their preparation are also described in said reference, and can be obtained commercially from Bibby Sterilin Stone, Staffordshire, UK.

It is also possible to use a combination of several different 3D-matrix sheets, for instance a nonwoven polyester sheet and a nonwoven polyurethane sheet, or a combination of a nonwoven and a woven structure. It is also possible to use a 3D-sheet with a varying density, i.e., a more open structure on the outside and a more compact structure on the inside, which can provide improved capture of cells during the loading of the bioreactor.

When used in the preferred form of a sheet or mat, said sheet or mat preferably has a thickness of 10 to 1000 $\mu$m, more preferably 250 to 750 $\mu$m, and usually around 400–500 $\mu$m and comprises round, flat non-round or hollow fibers or a combination of such fibers of the order of from 0.5 $\mu$m to 20 $\mu$m in diameter or width, preferably 10 $\mu$m to 15 $\mu$m and/or preferred derniers of between 0.05 and 5 dpf as described in said reference.

Said fibers are preferably disposed in the sheet or mat as a highly disordered, random like, intertangled manner, the axes of the fibers forming an open multi-dimensional array.

For use in the cultivation of liver cells and/or in the BAL-system of the invention, the thickness of the sheet is preferably about equal 0.2–0.8 mm, preferably around 0.5 mm.

Although not critical, the sheet will generally have a width of 10 cm to 100 cm, usually around 20 cm.

The oxygenating hollow fibers used in the solid support should be permeable to at least gaseous oxygen and/or gaseous carbon dioxide, and as such both porous and nonporous ("closed") fibers can be used, with porous fibers being preferred. In other respects, the molecular weight cut off of the fibers is not particularly limited.

The fibers can be made of any suitable material, preferably a hydrophobic material, such as silicone, polyethylene, polypropylene, hydrophobic polysulfone, or any other suitable hydrophobic material from which hollow fibers can be made, or any combination thereof.

Such fibers and their preparation are known in the art; suitable commercially available materials are Silastic from Dow Corning (silicone fibers), Oxyphan and Plasmaphan from Akzo-Nobel (hydrophobic polypropylene fibers), hydrophobic polysulfone fibers from Fresenius A. G., Bad Homburg, Germany, or polypropylene fibers coated on the inside and/or the outside with silicon rubber (Applied Membrane Technology, Minnetonka, Minnesota and Neomecs, St. Louis Park, Minn.).

The hollow fibers can be treated with gas-plasma before incorporation into the matrix material so as to improve their hydrophobic properties.

The outer diameter of the fibers is preferably less than 10 mm, more preferably 0.05–5 mm, more preferably 0.1–1.0 mm.

The fibers are preferably evenly distributed throughout the matrix material. More preferably, they are aligned in a parallel fashion running from one end of the matrix material to the other end thereby providing ease of construction of the solid support, without the need of forming a complex network of intertwining hollow fibers.

The number of hollow fibers and the distance between the individual fibers in the solid support will be such that all cells adhering to the matrix material are sufficiently provided with oxygen and with sufficient removal of carbon dioxide.

In order to achieve this the distance between the individual fibers, measured from the center of one fiber to the center of the next, will usually be less than 10 mm, more preferably 0.1–5 mm, even more preferably 1–3 mm and most preferably around 2 mm, total number of fibers being related to the total length of the fiber sheet. Preferably, the solid support comprises at least three, more preferably at least ten hollow fibers.

Usually, the reactor will contain 50 to 50,000, preferably 500 to 5000 hollow fibers.

Preferably, the hollow fibers are attached and/or physically bonded to said 3D-matrix material, although the invention is not limited thereto, and alternative embodiments will be described hereinbelow.

The fibers can be attached to the matrix material by means of any suitable method that does not impede the oxygen/carbon dioxide transport through the fiber wall. As such the fibers can be woven into the matrix material, glued onto the matrix material, sewn onto the matrix material, bonded thereon by means of ultrasound.

Examples of matrix materials suited in the practice of the present invention comprising hollow fibers attached to a nonwoven polyester sheet, comprise the commercial hollow fiber mats obtainable from Akzo-Nobel, (Wuppertal, Germany) and of Microgon (Laguna Hills, Calif., USA).

In order to improve bonding and/or not to damage the matrix material, the matrix material can first be laminated with a suitable polyamide or silicone sheet or a coarse polypropylene mesh as described in GB-A-2,178,447, after which the fibers are bonded to said sheet or mesh by the methods described hereinabove.

When the matrix material is in the form of a sheet or mat, the hollow fibers can be attached to both sides of the matrix material, but are preferably only attached to one side of the matrix mat.

According to a preferred embodiment, the general geometry of which is shown in FIG. 1, the matrix material of the invention consists of a 3D-polyester matrix 1 according to GB-A-2 178 447, provided with parallel hydrophobic porous hollow fibers 2 with a diameter of about 0.7 mm, that are spaced at a distance of about 2 mm, woven into the matrix material or bonded to one side thereof.

Figure 2:
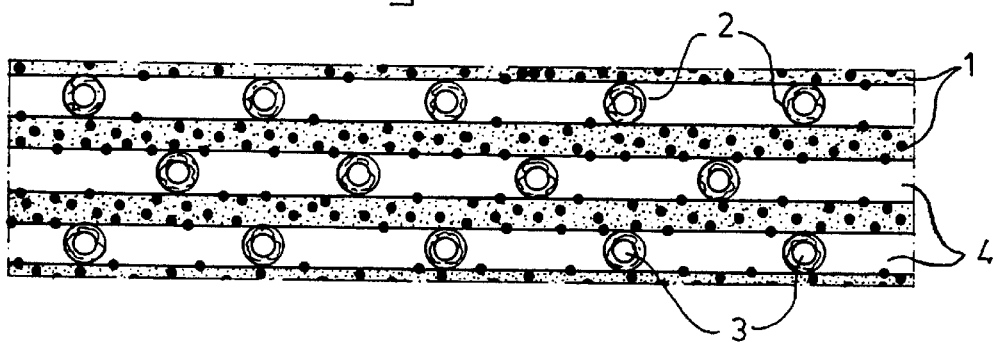
FIG. 2 shows a cross-sectional view of the preferred solid support of the invention in the "sandwich" configuration.

Such a solid support material provides ease of manufacture, and can advantageously be used in the "sandwich" configuration shown in FIG. 2, comprising a plurality of sheets 1, wherein each sheet is on both sides surrounded with the hollow fibers 2, and vice versa, with 3 being the intraluminal space (fiber lumen) and 4 being the extraluminal space.

In this sandwich configuration, besides providing for improved supply and removal of gases, the fibers advantageously also acts as a spacer between the individual fiber sheets, and serve as a baffle means and/or channeling means so as to provide for an uniform flow and distribution of the liquid medium through the extraluminal space 4 to all parts of the solid support.

Furthermore, the fibers 2 provide physical support to the matrix sheets 3, which is especially important when the solid support is to be subjected to high shear, such as a liquid flow.

When the sandwich configuration is used, it is possible that the fibers from individual layer to individual layer are at a slight angle to each other, or even perpendicular from layer to layer.

Figure 10:
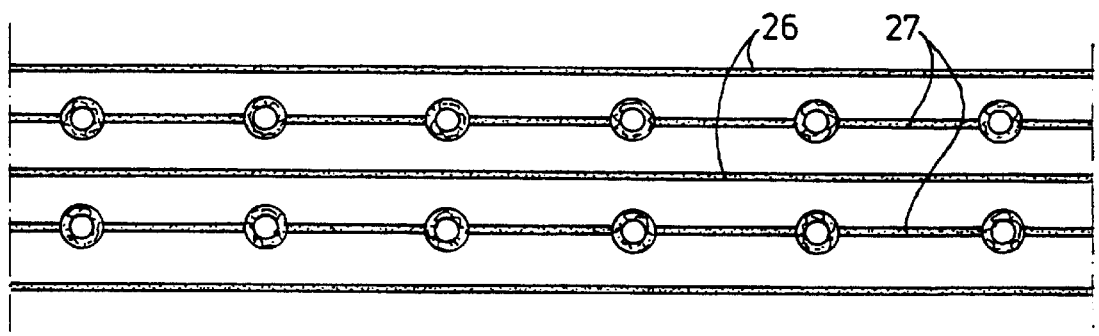
FIG. 10 shows an alternative embodiment of the solid support of the invention, comprising separate matrix sheets and hollow fiber sheets.

According to another preferred embodiment shown in FIG. 10, the solid support comprises a separate 3D-matrix sheet 26 and a separate fiber containing sheet 27, for instance obtained by weaving fibers into a sheet or bonding individual fibers together, and such sheets and their preparation are well known in the field of hollow fiber preparation.

In such a separate fiber sheet, the fibers can be parallel in one direction, or the sheet can comprise two, three or more sets of parallel fibers wherein the sets of parallel fibers are perpendicular or at an angle to each other. Such a sheet can for instance be obtained by weaving the hollow fibers in such a way that the desired number of hollow fiber sets as well as the desired angle between these sets is obtained.

In such a sheet comprising different sets of hollow fibers, the fibers can also be made of different suitable materials as mentioned hereinabove, dependent upon the final use of said set of fibers. They can also have different diameters, as long as they can be interwoven to form the desired hollow fiber sheet.

The fiber containing sheet can be laminated onto a sheet of the matrix material. It is also possible to attach the matrix material, for instance in the form of flakes, to such a hollow fiber sheet. All these embodiments are also preferably used in a sandwich configuration as shown in FIG. 10.

In all other respects, this embodiment comprises the same preferred aspects and advantages as mentioned hereinabove.

Finally, although the solid support of the invention generally does not require a pre-treatment step before use, such as the hollow fiber reactors of the prior art, it is within the scope of the invention to treat the entire solid support, or only the hollow fibers or hollow fiber containing mat, with extracellular matrix materials, such as Matrigel®, poly-N-para-vinylbenzyl-lactonamide or collagen based materials, in a manner known per se, in order to further improve cell adhesion. Also, the solid support can be provided with a sheet of an impermeable material such as polyamide, polyfluorethylene or silicone, for instance by laminating it onto the matrix sheet or rolling it up or stacking it with the solid support of the invention, thereby to some extent forming small compartments within the solid support for maintaining a homogeneous cell distribution.

Further advantageous embodiments will be clear to one skilled in the art and are comprised within the scope of the invention.

Geometry and Construction of the Bioreactor

In general the bioreactor of the invention comprises a suitable vessel, consisting of a wall enclosing a space, provided with the solid support of the invention.

The solid support is preferably in the form of a mat or sheet, more preferably in the "sandwich" configuration shown in FIG. 2. There are two preferred ways of obtaining said reactor geometry.

Figure 3:
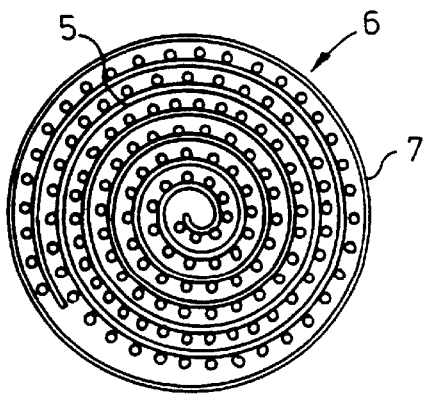
FIGS. 3 and 4 show two possible geometries of the bioreactors of the invention.

According to the embodiment shown in FIG. 3, the solid support 5 is present in the reactor 6 in the form of a spirally rolled-up mat or sheet of the matrix material, with 7 being the wall of the reactor vessel. According to this embodiment the reactor will usually be a cylinder.

Figure 4:
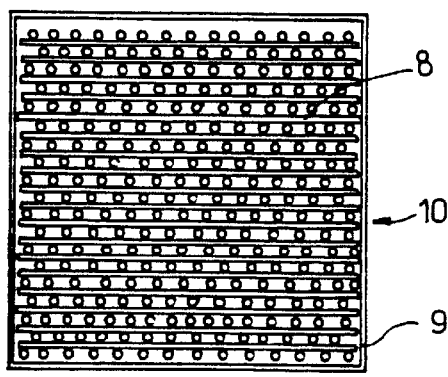

According to the embodiment shown in FIG. 4, the solid support 8 is present in the reactor 9 as stacked-up layers, with 10 being the wall of the reactor vessel. According to this embodiment, the reactor will usually have a box-like shape. Also, the individual solid support layers can be stacked at an angle, for instance at a right angles, giving the perpendicular hollow fiber configuration mentioned hereinabove.

The solid support/bioreactor of the invention can also comprise an alternating sheet of matrix material sheets and hollow fiber containing sheets as shown in FIG. 10, or hollow fiber sheets with the matrix material present in between the sheets, or bonded to the sheets, or comprise a laminate of a matrix material sheet and a hollow fiber sheet, as described hereinabove.

In all these reactor geometries, it is possible that there are incorporated into the support/reactor two, three or more separate sets of (preferably) parallel hollow fibers, wherein each set of fibers is at an angle or perpendicular to one or more of the other sets of fibers present in the reactor.

These different sets of fibers can be obtained by any of the methods described hereinabove, for instance by stacking individual layers of matrix material with hollow fibers physically attached thereto at an angle to each other, by using separate hollow fiber sheets comprising two, three or more individual sets of fibers at (an) angle(s) to each other as described hereinabove, by using separate sheets of matrix material and hollow fiber material and placing the hollow fiber sheets at (an) angle(s) to each other, or any combination thereof, such as the use of a sheet of matrix material with hollow fibers physically attached thereto stacked at an angle with a separate hollow fiber sheet.

When there are several sets of hollow fibers, these sets can be made from the same of different suitable hollow fiber materials and can have different diameters etc., dependent upon the final use of said fiber set.

Further suitable reactor geometries will be clear to one skilled in the art, and will be comprised within the scope of the invention. In any case the geometry will be such that during use all the cells in the bioreactor are in suitable proximity to the oxygenation fibers, so that they can be provided adequately with oxygen.

Also, for most applications, and especially for use as or in a BAL, the reactor geometry is preferably such that most or preferably all of the liquid medium perfused through the reactor vessel will come into contact with the cells immobilized on the solid support.

All the above mentioned reactor geometries comprising two or more sets of hollow fibers should however be distinguished from the reactor geometry described by Gerlach et al. comprising a three dimensional network of hollow fibers. In the Gerlach reactor, there is no separate 3D matrix material for cell adhesion, so that the cells have to adhere to the hollow fibers themselves. For this to be possible, the hollow fibers used in the Gerlach reactor have to be interwoven as such to form the required three dimensional network. Also, in this network, the distance between the individual interwoven hollow fibers must be so small so as to make three dimensional adhesion of the liver cells to these fibers possible. It will be clear that this will make the 3D hollow fiber network according to Gerlach et al. very difficult and expensive to produce.

According to the present invention, cell adhesion is essentially provided by the 3D matrix material, and not by the hollow fibers, so that a three dimensional hollow fiber network is not required for providing the 3D cell attachment. (For instance, in all the above reactor geometries, there is an essentially two dimensional hollow fiber network with the sets of fibers lying in the same—in the case of interwoven fiber sets—or in parallel—in the case of stacked fiber sets—plane(s) within the solid support).

It will be clear that because of this the distance between the individual hollow fibers in the solid support the invention is less critical and can be larger than in the Gerlach reactor, as long as sufficient oxygenation of all the cells present within the matrix can be obtained.

Also, the solid support of the invention with different sets of fibers is easier to manufacture simply by stacking or by using a two-dimensional fiber sheet comprising two or more sets of parallel fibers.

The reactor of the invention will usually comprise a gas inlet/outlet operably connected to the hollow fibers, so that gas can be fed to and removed from the hollow fiber lumen.

The reactor will usually also comprise at least one liquid inlet and outlet, operably connected to the extra fiber space, through which a liquid medium can be fed to or removed from said extra fiber space or the cells present therein. The reactor can comprise additional inlets and outlets for both gasses, liquids and/or solids, as required.

The reactor can further comprise all known elements of biological reactors, such as gas and/or liquid pumps operably connected to the different inlets or outlets; means for measuring and/or controlling the temperature within the reactor vessel; access means, such as a hatch, for accessing the inside of the reactor; inspection means; probes and means for inserting them, such as probes for the measurements of the viability as further described hereinbelow, etc.

The reactor may further be provided with means for the automatic control of the different reactor functions, such as a computer means operably connected with the pumps, temperature controlling means etc.

The reactor may also be provided with means for agitating the reactor, such as an electric motor, for instance for rotating the reactor along one of its axes, or with means for stirring inside the reactor, although the latter is usually not preferred.

The wall of the reactor vessel can be made of any suitable inert material, such as glass, plastics such as plexiglass, or metals, and polycarbonate or polysulfone, the latter materials being suited for the preferred steam sterilization. The inside of the reactor vessel can be provided with a special coating compatible with the cells to be cultured.

The size of the reactor is not limited and will usually depend upon the capacity required. The volume of the reactor can therefore vary from 1 ml to 1000 liters.

It will be clear, that for the above reactor geometries, the solid support of the invention, especially when used in the form of a sheet or mat with the hollow fibers attached to it, provides for ease of construction, especially compared to the capillary network containing the bioreactor of Gerlach et al. as described hereinabove. The solid support can also advantageously be used for adapting an existing reactor for use with the method of the invention.

For instance, the reactor geometry of FIG. 3 can simply be obtained by rolling up a sheet of the solid support of the invention and bringing said rolled up support sheet into the reactor vessel. It will be clear that the size of the solid support will be such that once rolled up, it will fit into, and preferably have a size essentially corresponding to, the size of the reactor vessel. If necessary the solid support can be cut to the desired size either before or after it has been rolled up. Similarly, the reactor geometry of FIG. 3 can be obtained by stacking up one or more sheets of the solid support of a suitable size, or folding one or more sheets into the reactor vessel.

As mentioned hereinabove, it is also possible to roll up a separate sheet of matrix material and a fiber containing sheet, or to stack up separate alternating layers of matrix material and fiber containing material.

In all these configurations, the hollow fibers will provide physical support to the rolled up or stacked up solid support, as well as provide for improved liquid flow through the extra fiber space.

It will be clear that in general, the amount of solid support present inside the reactor vessel as well as the dimensions thereof will usually be dependent upon and/or adapted to the volume and the dimensions of the reactor vessel.

The reactor vessel can also contain means for supporting and/or keeping in place the rolled up or stacked up solid support, as will be clear to one skilled in the art.

After the solid support has been put into place inside the reactor vessel, both the hollow fibers and the extra fiber space can be operably connected to the various gas inlets and outlets and fluid inlets and outlets, respectively, that will usually form part of the reactor vessel, optionally through or by means of distribution means that can provide for an even distribution of the gas flow and/or the liquid flow through the reactor.

According to the preferred embodiment of the invention, wherein the fibers are unidirectional, the fibers are on one side of the matrix material collectively connected to an gas inlet supply and on the opposing side collectively connected to a gas outlet. However, it is also possible to have a system working in countercurrent, i.e., where the direction of the gas flow is opposite from fiber (layer) to fiber (layer), or at right angles with the perpendicular configuration mentioned hereinabove.

It will be clear from the above that the reactor according to the present invention is also much easier to operate than reactor of Gerlach et al. comprising a woven network of four discrete capillary membrane systems, which therefore requires multiple inlet and outlet systems. Also, compared to the reactor of Gerlach et al., the solid support of the invention comprising a 3D-matrix material provides both improved cell attachment and improved cell capacity per unit volume.

According to the invention, the extracellular fiber space can be connected directly to a liquid inlet/outlet system, which makes it possible to perfuse said extra fiber space with liquid medium, giving direct liquid contact between the cells present in the extra fiber space and the liquid medium.

Although the invention in it simplest embodiment only comprises one set of hollow fibers for the supply and/or removal of gaseous components, it is to be understood that further separate hollow fibers systems for the supply and/or removal of specific gases and/or liquid media can be provided. These further systems can also be used for the separate controlled introduction of gaseous, liquid and/or dissolved components independent from the main gaseous or liquid feed as described hereinabove. It is also possible to use individual fibers, sets of fibers or fiber layers of the solid support for this purpose, as long as sufficient oxygenation can be maintained.

For such applications, the solid support/bioreactor of the invention will usually comprise two or more different sets of hollow fibers parallel of at (an) angle(s) to each other as described hereinabove, with each set of fibers being used for a specific purpose, with at least one set being used for sufficiently oxygenating the reactor according to the invention.

It is also possible according to the invention that different sets of hollow fibers are used for inflow and outflow. In this embodiment, the fiber will usually be closed at one end and at the other end be connected to an inlet or outlet respectively, said inlet and/or said outlet optionally being provided with pumping means.

The gaseous or liquid medium is supplied through the inlet to the fiber lumen of the inlet fiber, passes through the fiber wall into the extra fiber space and is then taken up by the outlet fiber and removed.

Although there may be problems with regard to the achievable flow and/or the fibers getting clogged, the main advantage of this embodiment will that all the medium supplied will necessarily come into contact with the cells in the extra fiber space.

Further advantageous embodiments will be clear to one skilled in the art and are comprised within the scope of the invention.

Cultivation of Cells in the Bioreactor

The bioreactor of the invention can be used to culture and/or maintain all kinds of cells, and the invention further relates to such uses and methods of cell cultivation and/or maintenance.

Preferably, the cells are plant, human or animal derived adherent cells, such as tissue cells, although fungal cells, as well as all kinds of one-cell organisms such as bacteria can also be cultivated with advantage.

The invention can also be used for the cultivation of modified cells such as cell lines, fused cells, hybridomas, transformants etc. Further examples of suitable cells will be clear to one skilled in the art.

The solid support and reactor of the invention can also be used for cultivating two or more different types of cells at the same time.

In general, the invention is especially suited for the cultivation of cells that put stringent requirements on the solid support available for cell attachment, the supply and/or removal of gaseous components, such as oxygen, or both. The advantageous properties of the solid support of the invention further make it possible to culture and/or maintain cells at very high cell densities and with excellent "three dimensional" cell attachment and cell proliferation, as mentioned hereinabove.

The total cell capacity of the reactor will usually be dependent upon factors like the size of the reactor, the amount of solid support present therein and the type of cells used.

In general, because of the very large surface area available for cell attachment, the improved oxygenation and the attainable high cell densities, the reactor will usually show a high cell capacity per unit volume. Also, because of the improved oxygenation and the homogeneous liquid flow, the reactor can be scaled up to the required capacity—for instance by increasing the volume and/or the amount of solid support present within the reactor in a manner known per se—without the problems of scale usually associated with large bioreactors, such as insufficient oxygenation and/or inhomogeneous liquid flow.

The reactor of the invention is especially suited for the cultivation of human liver cells or animal liver cells, such as dog or pig liver cells, both as primary cells or as immortalized cells.

The reactor can further be used for the cultivation and maintenance of liver-cell derived cell lines, liver cell transformants; and hepatoma cells and hepatoblasts, as well as cell lines derived therefrom, such as the transformed C3A-hepatoma derived cell line described by Sussman et al., incorporated herein by reference.

The term liver cells and/or the equivalent term hepatocytes as used in the present application therefore comprises all these different types of cells and cell lines.

Methods for obtaining said cells, such as isolation, culturing, transformation, etc., are well known and are for instance described in the abovementioned prior art, incorporated herein by reference.

Although for use in a BAL, preferably liver cells with a viability of more than 80% are used, for reasons mentioned hereinbelow, the BAL-system of the invention also makes it possible to use liver cells with a viability of no more than 70%, or even as low as 40–50%.

This means that the present invention puts less stringent requirements on the cell viability than the prior art BAL-systems that require a viability of more than 80%. This is an important practical advantage in view of the problems normally associated with attaining such high cell viabilities, especially with primary liver cells, as described hereinabove.

Furthermore, the invention makes it possible to use liver cells that have been stored by means of cryopreservation, which usually affords liver cells with a viability of less than 60–80%, so that the isolation of fresh liver cells with sufficient viability for each new BAL is no longer required. Again, this was not possible with the prior art BAL-systems.

If desired, the culture and maintenance of the liver cells can be carried out in the presence of added supplements such as growth factors, antibiotics and hormones, as well as added attachment factors and extracellular matrix constituents. These can be added to the perfusion flow itself before it enters the reactor of by means of separate means provided in the reactor, such as a separate set of hollow fibers provided for this specific purpose.

Also, the invention can be used for the co-culture of liver cells, for example with non-parenchymal liver cells. Optionally, this can be carried out in separate hollow fibers present in the reactor.

Although these techniques are known in the art, see for instance the abovementioned references, due to the advantageous properties of the solid support of the invention, their use is not always necessary and certainly not required.

The bioreactor can also be used for culturing hybridoma cells, i.e., for the production of monoclonal antibodies, which usually show poor attachment and/or adherence to solid supports.

For cultivating the cells, the cells are in general introduced into the bio-artificial reactor system, after which they are allowed to attach and/or adhere to the solid support during a suitable period of time. During this attachment phase, an oxygen-containing gas or gas mixture through the hollow fibers, such as pure oxygen, air, or a gas mixture containing oxygen, preferably 50–99% oxygen, more preferably 90–99% oxygen, in admixture with another inert and/or physiologically acceptable gas such as nitrogen or carbon dioxide is led through the oxygenating hollow fibers and spent gas is removed via the gas outlet.

Transport of these gases to the cells will essentially take place through diffusion, whereby sufficient gas exchange is assured both by the high available surface area of the hollow fibers as well as the small distance between the cells and the nearest oxygenating fiber. This diffusion-oxygenation avoids the limitations associated with oxygenation by the liquid medium, as well as the use of a separate oxygenator, because the oxygenator is directly incorporated into the reactor itself.

Also, nutrients can be fed to the attached cells, and waste products can be removed, in general by means of a extraluminal liquid flow. As such, all known and suitable nutrients and nutrient containing solutions and media can be used, or the solution can be especially adapted to the needs of the cells to be cultured.

Said nutrient medium is preferably fed from one side of the matrix material and removed from the other side, i.e., by means of an unidirectional flow, together with formed by-products and waste products.

It is also possible to provide separate fibers for the controlled feeding of some specific nutrients, although this will in general involve a more complicated construction and operation of the reactor, which for that reason is not preferred.

During cultivation, the cells can be kept at a desired, biologically or physiologically acceptable temperature, i.e., by keeping the reactor in a thermostat, or by controlling the temperature of the extraluminal liquid flow and/or the gas flow within the fibers, as will be clear to one skilled in the art.

In cultivating the cells, the reactor can be loaded with a small amount of cells, after which the cells are allowed to divide so as to fully populate the reactor. According to this embodiment, the solid support of the invention will require less heavy inoculation charges than prior art supports, with inoculations with amounts of 10% or less or even as low as 5% of the total cell capacity being sufficient so as to fully populate the reactor by advantageous "three dimensional" growth.

It is also possible to feed more cells into the reactor, so as to fully saturate the matrix material with adherent cells, or even to use an excess amount of cells, after which superfluous cells are removed.

Whether loaded with a small amount of inoculum, or with a large excess, the 3D-matrix support of the invention will provide for increased "capture" of the cells, so that cells with sub-optimal attachment can be used and/or the time needed for the attachment phase is considerably shortened. The latter is of special advantage when the reactor is to be used as a BAL, because the time needed until a BAL is ready for use is critical in a clinical setting.

Also, because of the extraluminal channels formed within the solid support by the hollow fibers acting as a spacer means, channeling means or baffle means, after introduction into the bioreactor, for instance by injection of a cell suspension, the cells will be distributed more quickly and more evenly over the entire support, reducing the time needed for the attachment phase even further and resulting in a more homogeneous cell distribution.

In general, the attachment phase will take from 30 minutes to 5 hours, dependent upon the specific cells used.

According to one special aspect of the invention, if the cell sample to be introduced in the reactor contains both viable and non-viable cells, the unique design of the reactor makes it possible to separate viable from non-viable cells, as will be described hereinbelow with reference to the cultivation of liver cells.

Further advantages of the bioreactor of the invention is that during the attachment phase the sedimentation of the cells as a large pellet on the bottom of the bioreactor can be precluded. This will also be further described hereinbelow.

After the attachment phase, and optionally a cell growth phase and/or the attainment of a steady state, the seeded reactor will generally be ready for its intended use. During such use, the cells will usually be maintained in/at sufficient quantity, viability and activity, i.e., by maintaining biologically and/or physiologically acceptable conditions, while the liquid medium to be treated is fed to the cells, usually through the extra fiber space. For most uses and with most cells, the bioreactor will make it possible to maintain viability and activity at higher levels during a longer period of time than prior art methods.

Although the invention will be further described hereinbelow with respect to the cultivation of liver cells and the use as a bio-artificial liver, it is expected that the bioreactor of the invention can also advantageously be used for other bio-artificial systems.

As such, the solid support and/or bioreactor of the invention can for instance be used in a bio-artificial pancreas, a bio-artificial kidney and/or a bio-artificial parathyroid gland, artificial bone marrow, systems that are currently based on hollow fiber reactors as described hereinabove. Use of the invention in these systems will also result in the advantages of the invention, such as improved cell attachment and capacity, direct contact of the cells with the liquid medium and/or improved oxygenation, as well as longer effective working time.

The bioreactor of the invention can also be used for the production, bioconversion and/or removal of substances in or from a liquid or gaseous medium, using cells capable of the desired biological reactions. For these and other applications, the invention advantageously provides for a high surface area available for gas exchange between the fiber lumen and the extraluminal space through the hollow fiber wall, as well as for direct liquid contact between the cells within the extracellular space and the liquid medium, the latter being of particular importance in the degradation, bioconversion or production of high molecular weight biological substances such as polypeptides. The produced substances can than be isolated from the liquid medium derived from the bioreactor in a manner known per se.

Other advantageous uses of the bioreactor of the invention will be clear to a man skilled in the art.

Use of the Solid Support and the Bio-reactor of the Invention as a Bio-artificial Liver As stated hereinabove, the advantageous properties of the solid support and the bioreactor of the invention make them especially suited for use in or as a bio-artificial liver system.

In such a system, suitable liver cells are cultured and/or maintained using the solid support and/or the bio-reactor of the invention as described hereinabove.

Therefore, in general, the bio-artificial liver system of the invention comprises a bioreactor of the invention and will as a rule also comprise liver cells as defined hereinabove, which usually will be present in the extraluminal space, more particularly be attached to the matrix material of the solid support.

During use, the bioreactor is operably connected to the blood circulation of a patient by means of a liquid circuit, so that a liquid medium directly or indirectly derived from the patient is fed to the liver cells in the extraluminal space, after which said cells are allowed to carry out most or all of the functions normally carried out by the liver in vivo. After treatment by the liver cells, the liquid medium is returned to the patient.

The BAL-system of the invention will therefore further comprise a liquid circuit for circulating the liquid medium, as well as pumping means known per se for controlling the liquid flow through said circuit. As such, the bioreactor of the invention can be incorporated into any such circuit known per se, for example as described in the abovementioned prior art, incorporated herein by reference, in which the bioreactor of the invention will replace, for instance, the hollow fiber BAL-system.

The circuit can also contain further means for the treatment of the liquid medium, such as an activated charcoal column for the absorption of hydrophilic toxins and/or a resin column for adsorption of hydrophobic substances (e.g., bilirubin).

The liquid circuit may also comprise cell filters for removing cells from the liquid flow. When used to keep dead liver cells away from the patient's circulation, this cell filter will usually be placed after the bioreactor.

The liquid circuit may also comprise means for adding nutrients and other desired substances to the liquid medium, although in this respect the liquid medium derived from the patient may itself be sufficient for keeping the liver cells in the reactor viable. Also, separate fiber systems for adding nutrients may be provided in the reactor as described hereinabove.

During use, the BAL-system of the invention can be perfused with whole blood—either arterial or venous—derived from a patient in a manner known per se. In this case the liver cells in the reactor need to be immunologically compatible with the patient's blood, so that usually human liver cells or cells and cell lines derived therefrom will be used. The less preferred use of xenocytes could require the use of immunosuppression.

However, the BAL of the invention is preferably perfused with plasma derived from a patient. In this preferred mode of plasma perfusion, the circuit will usually comprise a plasma separator or plasmapheresis unit for separating the plasma from the whole blood derived from the patient. The use of BAL-systems on the basis of plasmapheresis, as well as suitable plasmapheresis units, are well known in the field and are for instance described in the above prior art, incorporated herein by reference.

In its plasmapheresis mode, the circuit may also comprise immunological barriers for keeping the patient's blood circulation immunologically separate from the plasma circulation through the reactor, making it possible to use xenocytes such as pig hepatocytes without the need of immunosuppression. Usually, the plasma separator/plasmapheresis unit itself will provide to some extent for said immunological separation. The circuit can however also contain (further) separate means, such as membranes, columns or hollow fiber modules with a suitable molecular weight cut off, as described hereinabove, either placed before or after the reactor, and/or specific columns for the adsorption of antigens and/or antibodies etc. such as are known to one skilled in the art.

As mentioned hereinabove, a separate oxygenating unit does not have to be incorporated into the liquid medium circuit, even when plasma-perfusion is used.

A number of possible configurations of the BAL of the invention in the preferred plasmapheresis mode are shown in FIGS. 5–9.

Figure 5:
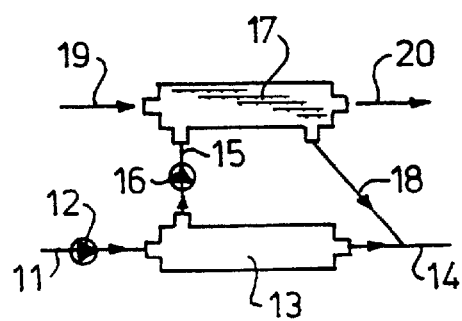
FIGS. 5 to 9 show four possible configurations of the bio-artificial liver system of the invention.

FIG. 5 shows a configuration in which arterial blood from the patient is fed through line 11, optionally by means of pump 12, to the plasmapheresis unit 13, where the plasma is separated from the whole blood, which is led back to the patient through line 14.

The plasma is then fed directly through line 15, optionally by means of pump 16 to the liver cells containing bioreactor 17, and from there returned to the directly venous blood in line 14 by means of line 18.

An oxygen containing gas is fed to the hollow fibers by means of feed 19, and the carbon dioxide enriched gas is led away through line 20.

Figure 6:
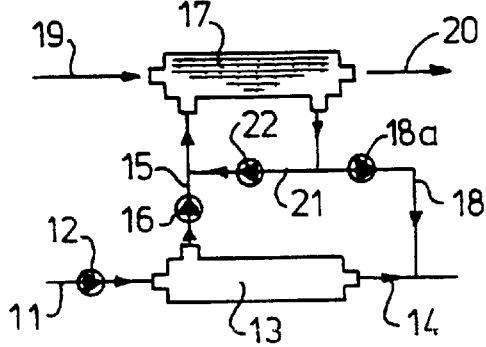

FIG. 6 shows a "high flow loop" configuration designed for recirculation of the plasma over the reactor by means of additional line 21 provided with pump 22.

Figure 7:
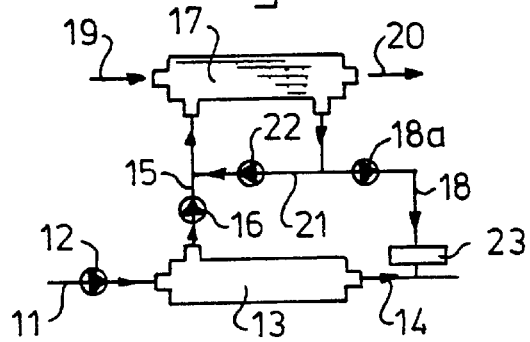

In FIG. 7, the circuit is provided with a cell filter 23 for keeping dead cells flushed out of the reactor away from the patient's circulation.

Figure 8:
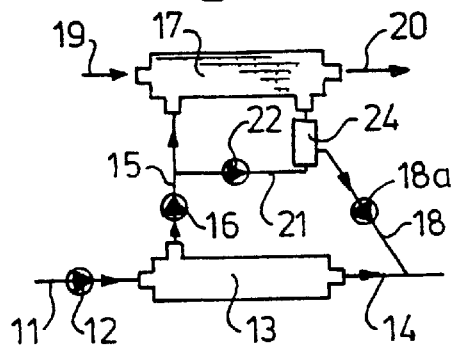

In FIG. 8, the circuit is provided with a hollow fiber membrane cartridge 24 for immunological separation placed in the high flow loop after the reactor.

Figure 9B:
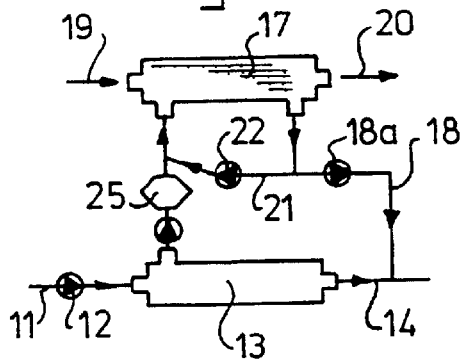
Figure 9A:
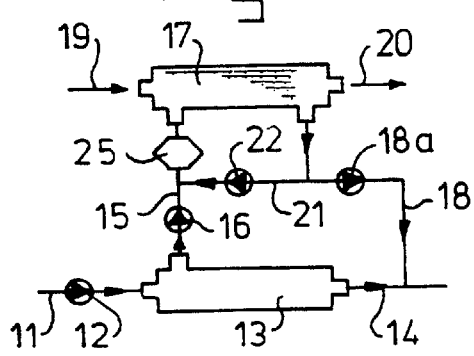

In FIGS. 9A and 9B the circuit is provided with an immunological pretreatment column and/or columns for hydrophilic and/or hydrophobic toxin removal, as described hereinabove step 25 either incorporated into (FIG. 9A) or outside (FIG. 9B) of the high flow loop.

It will be clear to one skilled in the art that all the different equipment mentioned above and shown in the figures can be combined into one circuit.

The different elements of the BAL-circuit may be provided as an integrated system in a single housing, or the BAL may consist of separate connected elements.

Although dependent upon the geometry and capacity, the amount and activity of the cells present in the reactor, the desired therapeutic application and other such factors, the BAL of the invention can be used to treat 1 to 300 ml of liquid medium derived from a patient per minute.

In order to achieve this, the liquid medium can be fed directly to the reactor 17 in at a corresponding rate, as shown in FIG. 5.

However, preferably the bioreactor of the invention is incorporated into a "high flow loop", as known per se from the abovementioned prior art, and shown in FIG. 6.

In such a loop, formed by reactor 17, line 21 and pump 22, and part of lines 15 and 18, as shown in FIG. 6, the flow of the liquid medium over the reactor 17 can be kept at a higher rate than the flow of liquid from the patient through lines 11 and 14, thereby providing for recirculation of the liquid medium over the reactor 17. Usually, this will be carried out by suitable control of pumps 16, 22 and 18a, by keeping them at a suitable flow ratio, usually from 1:2:1 to 1:100:1, respectively.

The BAL of the invention can also comprise two or more bioreactors of the invention connected in series and/or in parallel; for instance containing the same type and/or different types of liver or other cells.

The bio-artificial liver system of the invention can be used to support and/or replace liver function in patients with impaired liver function and/or in cases in which artificial liver support is desirable and/or required. The BAL-system can for instance be used in patients suffering from fulminant hepatic failure (FHF), for instance due to viral hepatitis infections or acute liver poisoning (for instance with acetaminophen, $CCl_4$, alcohol or drugs), as well as transient liver ischemia, and liver trauma due to injury. The artificial liver can also be used to improve the patient's condition before liver transplant, to bridge the period before liver transplant, to bridge the rejection period after acute rejection of a transplanted liver, during the anhepatic phase while a liver transplant is carried out and/or during recovery of a liver transplant, or to allow time to regenerate the patient's own liver.

Furthermore, the BAL system of the invention can be used in the treatment of chronic liver diseases to enhance the quality of life of the patient and/or to bridge periods of exacerbation.

The BAL-system of the invention can also be used to bridge patients through a relatively brief crisis period allowing their own livers to regenerate thereby sparing the trauma and expense of transplants.

As such, the BAL of the invention will preferably be used continuously, although intermittent use is also envisaged.

In order to obtain the bioreactor, the liver cells can be introduced into the bioreactor in a manner known per se and/or as described hereinabove.

According to one embodiment, only a small number of cells is seeded into the reactor, after which said cells are allowed to grow and divide, until the bioreactor has reached its maximum capacity and/or a steady state is reached after which the reactor can be used as a BAL.

In this embodiment, the support and bioreactor are therefore used for cultivation of the liver cells as well as the bio-artificial liver system itself. It will be clear to that according to this aspect of the invention, the 3D-solid support of the invention will favor cell growth and cell division, especially compared to the hollow fiber systems of the prior art, in which cell growth and division will usually be limited or even precluded.

This embodiment will usually not be suited for liver cells that are unable to divide and grow after they have been isolated, such as primary liver cells. It is however expected that even with primary liver cells, the solid support of the invention will favor some growth and division, especially compared to the prior art. The cultivation of primary liver cells using the solid support and/or the bioreactor of the invention, optionally with the use of growth factors etc., is therefore expressly included within the scope of the present invention.

According to another embodiment, the amount of cells will largely correspond to and/or exceed the capacity of the bioreactor. In this case the cells are added to the reactor and allowed to adhere to the solid support, after which the excess non-attached cells are removed, for instance by washing. After that, the bioreactor can be used as or in a BAL, optionally after attainment of a steady state.

This embodiment will generally have the advantage that the BAL-system is ready for use after a shorter period of time compared to prior art systems, according to the invention usually between 0.5 to 6 hours, in most cases around 2 hours. Also, this embodiment is especially suited for use with primary liver cells.

In general, the BAL will be seeded with $1 \times 10^5 - 1 \times 10^8$ cells/ml, usually around $1-50 \times 10^6$ cells/ml (unit volume), and to a total capacity of $10^8$ to $10^{11}$ cells, i.e., around 1–1000 g cells, preferably 100–500 g cells.

The reactor is usually seeded by injecting a suspension of the liver cells into the reactor, obtained for instance by cultivation of the cells, by suspending liver cells in a suitable liquid medium, or after isolation, after which the cells are allowed to distribute themselves throughout the reactor and adhere themselves to the solid support during a suitable period of time, usually from 1 minutes to 5 hours or more, preferably about 30 minutes to 3 hours, and more preferably around 2 hours. For comparison, with the reactor of Gerlach et al., the attachment phase can take up to 8 hours or more.

In order to facilitate the distribution of the cell suspension even further, the reactor can be agitated after the cell suspension has been injected.

Figure 11:
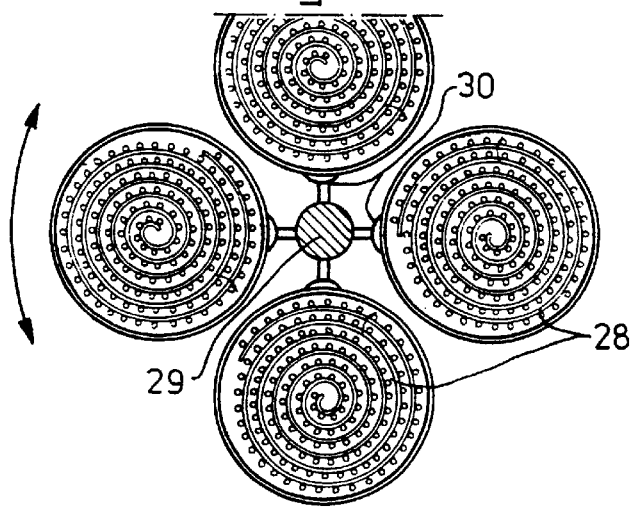
FIG. 11 shows schematically an apparatus for immobilizing cells within the bioreactor of the invention.

According to a highly preferred embodiment, after injection of the cell suspension, the reactor is rotated, intermittently but preferably continuously, around its longitudinal axis, i.e., the direction of the hollow fibers in the solid support, during the abovementioned period of time at a speed of 0.01–100 rpm, preferably 0.1–10 rpm, more preferably around 1 rpm. In the preferred embodiment shown in FIG. 11 the bioreactor 28 shown in FIGS. 3/4 is rotated around a central axis 29, the reactor being attached to the axis by means of attachment means 30, such as a clamp of suitable size (not shown).

This method of distributing the cells throughout the reactor prevents the formation of a cell pellet at the bottom in the bioreactor, which would lead to mass transfer problems during use, especially with regard to the cells at the center of the pellet, which can lead to loss of functional activity and/or viability. By rotating the reactor, and preferably periodically reversing the direction of rotation, the direction of sedimentation continuously changes, and the cells in suspension can be considered to follow an almost circular path through the reactor, so that the cells repeatedly come into contact with the matrix material, thereby greatly enhancing the chances of entrapment by the polyester fibers in said matrix material, so that a homogeneous immobilization at a high rate and speed of attachment is obtained.

After immobilization of the cells is complete, the remaining suspension containing non-adhered and/or excess cells is removed from the reactor, after which the reactor can optionally be flushed and/or with a suitable liquid medium.

Also, by agitating, and preferably rotating the reactor, living cells can be separated to at least some extend from dead cells present within the injected cell suspension, especially when a cultured suspension of primary liver cells is used. The living cells are entrapped by and/or adhere to the solid support, whereas the non-adhering dead cells are removed with the remaining suspension or by washing the reactor.

Also, by perfusing the reactor with a suitable liquid medium, dead cells can be flushed out of the reactor. This "flushing out" of dead cells can even take place during use, i.e., while the reactor is connected to the perfusion circuit. In this case, incorporating a cell filter 23 into the liquid circuit after the reactor, as shown in FIG. 7, will be highly advantageous.

This favorable removal of dead cells cannot be achieved with the prior art hollow fiber bioreactors, because in these reactors, the liver cells essentially are present in an enclosed "compartment" between the hollow fibers, without means for perfusing said space, or captured within a (hydro)gel.

During use, the liver cells in the reactor are maintained in a manner known per se. The BAL of the invention is preferably kept at a physiologically acceptable temperature, preferably around 37° C. Also, additional nutrients and other suitable substances may be added to the reactor, as and if required.

The liver cells are oxygenated by feeding an oxygen or an oxygen enriched gas such as "carbogen" (a 95:5 $O_2/CO2$ mixture) or a $CO_2$-enriched oxygen containing gas, such as "culture gas" (95% air, 5% $CO_2$). This gas can be fed by any suitable means, such a gas-cylinder or a gas pump, or by connection to an external gas supply. As stated hereinabove, this method of direct oxygenation through closely packed hollow fibers means that the generation of deleterious oxygen and/or carbon dioxide gradients is avoided. Also, during perfusion, the liquid medium used can have a further "mixing" action on the gas supply, reducing said gradients even further.

Before or during use, the functional effect and the metabolic performance of the bioreactor and the cells contained therein can be monitored in a manner known per se with any of the large number of tests available for this purpose, such as measurement of protein synthesis, ureagenesis, oxygen uptake (for which advantageously direct measurement at the gas inlet and gas outlet can be used), cytochrome P450-activity, drug metabolic assays, clearance techniques etc., see for instance Rozga et al., mentioned hereinabove and incorporated herein by reference. Also, a biomass meter (Aber) can be used, which uses conductivity measurements based upon differences in membrane potential between dead cells and living cells. Such a meter is known to one skilled in the art.

The use of the bio-artificial liver of the invention will of course afford all the advantages associated with the use of the solid support and the bioreactor of the invention, as well as a number of further advantages, such as:

Improved attachment of the liver cells and improved cell capacity per unit volume due to the presence of a suitable matrix material. The solid support also offers an improved environment for cell growth and cell division.

Improved oxygenation of the liver cells due to the presence of the oxygenation fibers, without the need of a separate oxygenator and without the occurrence of deleterious gradients.

Direct liquid contact between the liver cells and the blood or plasma to be treated, without the need for toxins and/or liver secretions to pass a membrane with the associated mass transfer and molecular cut off problems.

The reactor can easily be "scaled up" to the capacity required for therapeutic use.

A simple construction that can easily be manufactured and operated, in its simplest form requiring only one fluid inlet/outlet and one gas inlet/outlet. Also, no expensive pre-treatment of the solid support is required.

Compared to the prior art systems, the bioreactor of the invention puts less stringent requirements on the (primary) liver cell preparations used, especially with regard to viability and attachment.

The speed and rate of cell attachment after seeding is reduced, so that the time until the BAL is ready for use is shortened and less liver cells are required.

Finally, a major advantage of the use of the 3D-solid support and the bioreactor of the invention as a BAL and/or in the cultivation and/or maintenance of liver cells, as well as the abovementioned rotation method for seeding the reactor, is that the cells will be present and/or maintained in the reactor as small cell aggregates, in at least one diameter not being larger than 10 cells, preferably being not larger than 6–8 cells (100 $\mu$m). It is well known in the art that such hepatocyte aggregates function and remain viable during a longer period of time, are more active and better differentiated than hepatocytes grown in monolayers or on 2D-carriers or hollow fibers. Also, the morphology of the cells cultured in such small aggregates is similar to the morphology of liver cells in the liver in vivo. Also, as these aggregates are of relative small size (only 6–8 cells in diameter) there are no problems with regard to mass transfer to the cells at the center of the aggregates, as with liver cells cultured in large (>than 200 $\mu$m) aggregates, such as the 500 $\mu$m aggregates in the reactor by Gerlach et al., or immobilized in microcapsules.

The invention therefore makes it possible to cultivate liver cells in a high capacity reactor at very high cell densities, i.e., 20–40×$10^6$ cells/ml or more. It can also be said that, in general and compared to the BAL-systems of the prior art, the solid support of the invention provides an environment that more closely matches the biological conditions/environment of the cells in the liver.

Of course, these characteristics also mean that the BAL of the invention has great advantages from a therapeutic point of view, especially compared to the prior art systems. The BAL will generally be therapeutically effective for a longer period of time, show improved efficiency and can be easily provided with sufficient capacity for liver replacement.

A further practical advantage of the BAL of the invention is that it can be sterilized in an autoclave (20 minutes at 120° C.). Prior art systems require gas sterilization with toxic gases such as ethylene oxide, which is still present in and given off by the reactor fibers weeks after the reactor has been sterilized.

Finally, the BAL of the invention for the first time makes it possible to successfully employ cryopreserved primary hepatocytes in a bio-artificial liver system, opening the possibility of centralized isolation and preservation, after which the cells can be distributed to the hospitals where they can be stored until they are needed. Together with the shortened attachment phase of the BAL of the invention, this means that in a clinical setting, the BAL of the invention can be put at the disposal of physician sooner and at lower costs.

The invention will now be illustrated by means of the following non-limiting examples.

EXAMPLE I

In Vitro Tests

The development of a liver support system for the treatment of patients with fulminant hepatic failure and as a bridge to liver transplantation is a significant challenge. Many early attempts focused on blood detoxification based on the assumption that liver failure could be reversed if the associated toxins were removed from the circulation of the patient. Although improvement of the neurologic status in patients has been reported, none achieved long-term survival. It was therefore concluded that an effective liver support system should be able to perform the liver's multiple synthetic and metabolic functions, including detoxification and excretion. The most logic approach to this problem is the introduction of active functioning hepatocytes. The state-of-the-art embodiment of this theory is presented in the bio-artificial liver (BAL), an extra-corporeal device comprising well nourished and oxygenated viable hepatocytes immobilized on a mechanical support and separated from the blood circulation by semipermeable membranes.

Objectives like biocompatibility, maintenance of functional capacity and practicality, important aspects in the development of the BAL, have been discussed in the prior art. However, the current bioreactor designs do not meet the essential conditions for optimal mass transfer to and from the hepatocytes as present in the intact liver. In this respect, the impact of the bioreactor construction on hepatocyte function has been undervalued.

The aim of our study was to develop a bioreactor configuration that allows high density hepatocyte culture and simultaneously ensures every hepatocyte to operate under in vivo like perfusion conditions and direct medium contact, thereby more closely mimicking physiological mass transfer. In addition, we wanted to culture hepatocytes as small aggregates, known to maintain many of the cyto-architecture characteristics found in vivo and exhibit higher and prolonged functional activity compared with hepatocytes cultured as monolayers.

Another goal was to develop a bioreactor which can be scaled up to incorporate sufficient cell mass for therapeutic liver support. This resulted in a novel bioreactor design comprising a spiral wound 3D nonwoven polyester matrix and an integrated oxygenator in which hepatocytes reorganize and immobilize as small aggregates.

Hereinbelow, the characteristics and the in vitro results of the novel bioreactor design of one embodiment of the invention are presented.

MATERIALS AND METHODS

Hepatocyte Isolation

Pig livers were kindly provided by the department of clinical and experimental cardiology of the AMC, Amsterdam, the department of dermatology of the AMC, Amsterdam, and a local slaughterhouse. The hepatocytes were isolated from pigs with a body mass of 20–25 kg using a simple two step collagenase perfusion technique as described previously (te Velde AA, Ladiges NCJJ, Flendrig LM, Chamuleau RAFM, J Hepatology 1995; 23:184–192, incorporated herein by reference.). The viability of the isolated cells based on trypan blue exclusion varied from 71 to 96% (n=8, mean 89±7%). The yield varied from $8 \times 10^6$ to $30 \times 10^6$ hepatocytes per g wet liver weight for the different isolations.

Bioreactor

The bioreactor is based on a 3D nonwoven polyester fabric especially designed for culturing anchorage dependent cells (Bibby Sterilin Ltd, Stone, Staffordshire, GB) and hydrophobic polypropylene hollow-fibers donated by Dr. J. Vienken of Akzo-Nobel (Plasmaphan, Akzo-Nobel, Wuppertal, Germany) for oxygenation and carbon dioxide removal. The 3D-fabric (dimensions: length 140 mm, width 90 mm, thickness 0.5 mm, fiber diameter 13 $\mu$m) provides a scaffold for hepatocyte immobilization and self-aggregation. Its surface for attachment is about 15 times its projected area which enables high density hepatocyte culture. The oxygenation hollow-fibers (external diameter 630 $\mu$m, internal diameter 300 $\mu$m) are fixed to the 3D-carrier in a parallel fashion by weaving, spaced at an average distance of 2 mm. In general, this is carried out by folding the matrix material three or more times, making a number of holes in the folded matrix material spaced 2 mm apart by means of a needle, putting the hollow fibers of suitable length through the holes thus obtained, and then again stretching the folded matrix material in the direction of the fibers so as to remove the folds, giving a matrix material with the hollow fibers oriented in a unidirectional parallel fashion.

This polyester-polypropylene composite is spiral wound like a Swiss roll with the help of an acrylic core (FIG. 3) and placed in a polysulfone dialysis housing (Minifilter, Amicon Ltd, Ireland, ID 1.4 cm, ED 1.7 cm, total length 15.5 cm). The oxygenation hollow-fibers are embedded in polyurethane resin (PUR-system 725 A and 725 BF, Morton International, Bremen, Germany) using dialyzer potting techniques and fitted with gas inlet and outlet endcaps.

Figure 12:
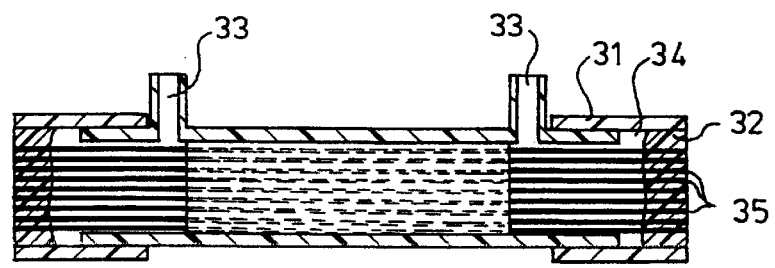
FIG. 12 shows schematically a possible construction of a bioreactor of the invention.
Figure 13:
FIG. 13 shows a light microscopic photomicrograph of a cross-section of the 3D-matrix from a hepatocyte bioreactor cultured at $20 \times 10^6$ viable cells/ml for five days.

The resulting bioreactor is shown in FIG. 12, with 31 being the housing, 32 being the polyurethane potting, 33 being the extra fiber space inlet and outlet, respectively, 34 being the extra fiber space and 35 being the hollow fibers.

The bioreactor is sterilized by autoclaving (20 min. at 121° C.). Hepatocyte seeding in the extra fiber space (volume 11 ml, suited for future in vivo experiments in the rat) is realized by injecting the cell suspension via the inlet and outlet ports normally used for dialysate flow. The same ports are used for medium perfusion after cell immobilization.

Hepatocyte Culture

Hepatocytes suspended in ice cold Williams' E medium (Gibco BRL Life Technologies, European Division) supplemented with heat inactivated FCS (10%, Boehringer Mannheim), glutamin (2 mM, BDH Laboratory Supplies Ltd.), insulin (20 mlE, Novo Nordisk, Denmark), dexamethason (1 $\mu$M) and antibiotic/antimycotic solution (Gibco) at a concentration of $20 \times 10^6$ viable cells/ml were injected into two precooled (4° C.) dry bioreactors to a final amount of $220 \times 10^6$ cells/unit. The cooled bioreactors were integrated into two separate cell perfusion circuits to obtain results in duplicate. This setup was put in a temperature regulated (37° C.) cabinet (Stuart Scientific, model SI60, GB) where the bioreactors were clamped onto a rotation device according to FIG. 11 and connected to culture gas (95% air, 5% $CO_2$, gas flow: 30 ml/min., 37° C.). The reactors 28 were rotated horizontally along their longitudinal axis 29 at 1 revolution/min. for a period of 120 minutes to secure an even distribution of the cells throughout the reactor and to accelerate immobilization by entrapment, attachment, and self-aggregation of viable hepatocytes. Every minute the rotation direction was reversed automatically to prevent the connecting tubing from knotting. After this immobilization period an 15 hour intermittent fresh medium waste wash was performed (60 ml) to flush dead and unattached cells out of the reactor, to supply nutrients to and remove toxins from the cell region, and allow the hepatocytes to recover from the isolation procedure. Then, the devices were ready for use.

Hepatocyte Function Tests

General Description

The study included bioreactors with and without hepatocytes, the latter serving as controls. Both groups received identical treatment and monitoring. The hepatocyte function tests were performed under recirculating conditions, perfusing supplemented Williams' E medium (30 ml) through the extra fiber bioreactor space at a flow rate of 5 ml/min. Various parameters were assessed over a period of 4 days, the last day exclusively reserved for protein secretion under serum free conditions. On every day during the first three days a battery of tests was carried out including, galactose elimination, urea synthesis, lidocaine metabolism, and a subsequent 14 hour incubation with supplemented Williams' E medium to evaluate the amino acid metabolism, lactate/pyruvate ratio, enzyme leakage, glucose levels and pH. Every test was preceded by a fresh medium waste wash. Samples collected from the closed loop circuit were snap frozen in liquid nitrogen and stored at −70° C. prior to analysis.

Galactose Elimination

D-Galactose (Sigma Chemical Co., St Louis, Mo.) was administered to the closed loop circuit at a concentration of 1 mg/ml and incubated for 3 hours. Media samples were collected at different times every day for three days. The galactose concentration was measured at 340 nm (Cobas Bio, Roche, Switzerland) using enzymatic test kits (Boehringer Mannheim, Wiesbaden, Germany, kit no. 124273). From this the galactose elimination was calculated.

Urea Synthesis from $NH_4Cl$

The urea synthesizing capacity of the bioreactor system was assessed by incubating 10 mM $NH_4Cl$ for 2 hours. Media samples were collected at different times every day for three days. Urea was determined calorimetrically at 525 nm (Zeiss UV spectrophotometer) with Sigma Chemical Co. kit no. 535 for urea nitrogen.

Lidocaine Metabolism

Lidocaine-HCl (Sigma) was administered to the closed loop circuit at a concentration of 500 $\mu$/ml and incubated for 1 hour. Media samples were collected at different times every day for three days. The samples were analyzed for lidocaine and three lidocaine metabolites, mono-ethyl-glycine-xylidide (MEGX), 2,6-Xylidine-HCl, glycine-xylidide (GX), by reversed phase high performance liquid chromatography (HPLC). Lidocaine-HCl was obtained from Sigma Chemical Co. and MEGX, Xylidine, GX, and ethyl-methyl-glycine-xylidide (EMGX) were gifts from Dr. R. Sandberg of Astra Pain Control (Södertälje, Sweden).

Sample preparation for the analysis of MEGX, Xylidine and GX involved addition of an 75 $\mu$l internal standard solution (EMGX 5 $\mu$g/ml in aqua dest.) and 150 $\mu$l aqua dest. to a 150 $\mu$l sample. Analysis of the much higher lidocaine concentrations required a 20-fold dilution of the sample in supplemented Williams' E medium. The isolation of lidocaine and its metabolites was performed by extraction. For this, 150 $\mu$l sodium carbonate (0.1 M) and 600 $\mu$l chloroform were added. After 1 min. vortexing and 4 min. centrifugation at 8000 rpm the aqueous supernatant was removed and 150 $\mu$l aqua dest. and 350 $\mu$l HCl (0.1 M) were added to the organic phase. The vortexing and centrifugation procedure was repeated and the supernatant removed. A cooled sample storage compartment kept the residues at 4° C. prior to analysis. The mobile phase (0.5 M phosphate buffer, pH 4.5) was pumped at a flow rate of 1.7 ml/min. (Perkin Elmer 250) and pretreated by a Quard-column (Superspher 60 RP 8, length 10 cm, 4 $\mu$m particles, Bischoff Chromatography, Germany). An auto sampler (Gilson Sample Injector model 231, France) injected 50 $\mu$l aliquots onto a temperature regulated (55° C., Chrompac Column Thermostat, The Netherlands) HPLC column (Superspher 60 RP 8, length 20 cm, i.d. 4.6 mm, 4 $\mu$m particles, Bischoff Chromatography, Germany). Detection was at 198 nm (Schoeffel SF 770 UV-spectrophotometer, Germany) and peak areas were calculated with the aid of an Olivetti M250 computer utilizing integration software (Chrompac PCI, version 5.12, The Netherlands). The samples were quantified by comparing the peak area ratio of the component of interest to that of the internal standard. Standard curves were obtained for lidocaine (5–80 $\mu$g/ml), MEGX (0.5–16 $\mu$g/ml), Xylidine (5–80 $\mu$g/ml) and GX (1–32 $\mu$g/ml) and showed linearity (r=0.996, n=6). The detection limit was 0.4 $\mu$/ml for GX, 0.3 $\mu$g/ml for Xylidine, 0.2 $\mu$g/ml for MEGX, 0.4 $\mu$g/ml for EMGX and 0.5 $\mu$g/ml for lidocaine and the retention times were 2.2 min., 2.4 min., 3.2 min., 4.1 min., and 5.8 min., respectively. Column stabilization time was limited to 20 minutes by washing with a phosphate/acetonitrile/phosphoric acid buffer (50 mM, pH=1.7) and an acetonitrile solution (aqua dest.:ACN=1:1) to remove the chloroform peak.

Amino Acid Metabolism

The metabolic turnover of a wide range of amino acids was investigated. The amino acid concentrations were determined by a fully automated precolumn derivatization with o-phthaldialdehyde (OPA), followed by high-performance liquid chromatography as described in van Eijk HMH, van der Heijden MAH, van Berlo CLH, Soeters PB, Clin Chem 1988; 34:2510–13.

Lactate/Pyruvate Ratio

The lactate/pyruvate levels were determined at 340 nm (Cobas Bio, Roche, Switzerland) by enzymatic test kits (Boehringer Mannheim Wiesbaden, Germany, lactate kit no. 149993 and pyruvate kit no. 124982). From this the lactate/pyruvate ratio was calculated.

Enzyme Leakage

Lactate dehydrogenase (LDH), glutamic oxaloacetic transaminase (GOT) and glutamic pyruvic transaminase (GPT) levels were measured by routine clinical analyzers.

Glucose

Glucose levels were measured using glucose test strips (hemoglucotest 1-44 R, Boehringer Mannheim, Wiesbaden, Germany) and the accessory Reflolux-S readout device.

pH

The pH was measured by sampling 1 ml of medium with a bloodgas syringe (Marz-175, Sherwood Medical, Ireland) which was determined on a bloodgas analyzer (Radiometer, model ABL 300, Copenhagen).

Protein Secretion

On day four the entire bioreactor culture system was washed with 250 ml supplemented Williams' E medium without FCS and incubated in the same medium. Media samples were collected after 24 hours and dialyzed extensively against a 50 mM $NH_4HCO_3$ solution and frozen dried. The dry residues were reconstituted in such an amount of electrophoresis buffer (Tris-barbital buffer, pH=8.6, ionic strength 0.1) that the culture supernatant was concentrated 20 times.

To visualize the serum proteins secreted by the pig hepatocytes we performed crossed-over immunoelectrophoresis using a polyspecific antiserum to pig serum proteins as described previously (28).

Microscopic Examination

Five day old culture systems were prepared for microscopic examination to determine the orientation of the hepatocytes in the bioreactor.

Light Microscopy

The hepatocytes were fixed by flushing the bioreactor with formalin (4%). After 24 hours the bioreactor was cut open and twelve matrix samples (1 $cm^2$) were taken from various parts of nonwoven fabric. The samples were washed in water, dehydrated in graded ethanols, and embedded in paraffin. From this 8 μm thick slices were cut, which were deparaffinated with xylol and colored with haematoxylin-eosin. The preparations were observed under an Olympus Vamox light microscope (type AHBT3, Tokyo, Japan).

Scanning Electron Microscopy

The hepatocyte aggregates from five day old cultures were fixed by flushing the bioreactor with 4% glutaraldehyde in phosphate buffer, pH 7.3 (Fluka Chem A.G., Buchs, Switzerland). The bioreactor was cut through in the middle and one part was dehydrated in graded ethanols and finally dried in hexamethyldisilizane (Sigma, Munchen, Germany). The cut surface was coated with gold in a sputter coater and observed under a scanning electron microscope (ISI SS40, Japan).

Statistical Analysis

An unpaired Student's t-test was used, and $P<0.05$ was considered to be statistically significant. Data were presented as mean±SEM.

Magnetic Resonance Imaging (MRI)

MRI is a non-invasive method for visualizing the liquid flow distribution in for instance a tube, or in the case of the present invention, the bioreactor.

The flow distribution in a cross-section of a small (ID 1.32 cm, volume 11 ml, 46 hollow fiber membranes, diameter acrylic core 0.4 cm) and a scaled-up bioreactor (ID 2.2 cm, volume 33 ml, 138 hollow fiber membranes, diameter acrylic core 0.4 cm) of equal length was investigated. First, the bioreactors were flushed with ethanol and subsequently water to remove air bubbles which can block the medium flow and/or can distort the homogeneity of the magnetic field resulting in a decreased signal intensity. A bioreactor was then placed in a birdcage coil and positioned horizontally in a 6.3 Tesla/20 cm bore home built spectrometer. Cell free devices were used as the spectrometer was not equipped to support viable hepatocytes. Transaxial flow sensitive MRI's were taken from the middle of the bioreactor using a novel steady state perfusion imaging technique. Briefly, the water signal in a detection slice (width 2 mm, perpendicular to the flow direction) is suppressed. During an in-flow time of 100 ms, part of the slice is refreshed resulting in an increase in signal intensity. So, the higher the flow, the more the detection slice is refreshed, the more the signal intensity will increase. Fluid flow at higher velocities than 2 cm/s will not result in an increased signal, as the detection slice is then completely refreshed. Therefore, the flow was calibrated such that the maximum fluid velocity in most flow channels did not exceed 2 cm/s.

Alpha-GST Assay

Toxic Serum and Hepatocyte Viability

Alpha-GST is released by hepatocytes with a damaged cell membrane, and is therefore a marker for the integrity of the hepatocytes. The liver enzyme alpha-GST was determined species specific (rat, pig, human) with an ELISA kit provided by Biotrin, Ireland.

Rats with liver ischemia were treated with a porcine hepatocyte based BAL. Plasma samples were collected in time to determine the rat and pig alpha-GST levels (in one and the same sample).

RESULTS

Hepatocyte Culture

The study included 22 bioreactors, of which 16 devices (n=8 in duplicate) were used to culture hepatocytes and 6 devices without cells (n=3 in duplicate) served as controls. The results of the hepatocyte function tests in two bioreactors with cells from the same isolation procedure never differed more than 10%, indicating reproducible cell immobilization and cultivation. The culture system remained sterile throughout the study and no leaking of medium into the lumen of the oxygenation hollow-fibers was observed.

Hepatocyte Function Tests

Galactose Elimination

The galactose elimination capacity after incubation for 180 min. with a standard dose of galactose remained constant over a period of three days.

Urea Synthesis

High levels of ammonia play a role in hepatic encephalopathy. Synthesis of urea from ammonia is therefore an important function test. Urea synthesis after a 120 min. incubation with 10 mM $NH_4Cl$ did not vary over a period of three days.

Lidocaine Metabolism

The cytochrome P450 activity of the hepatocytes was assessed by determining lidocaine and its metabolites.

The lidocaine elimination and subsequent MEGX and Xylidine production after a 60 min. Lidocaine incubation did not significantly change over a period of three days. Xylidine was the main lidocaine metabolite on the first two days. There was no significant difference in Xylidine and MEGX production on day 3. When looking at individual experiments, lidocaine clearance correlated better with Xylidine than MEGX formation. Porcine hepatocytes did not produce detectable levels of the metabolite GX during incubation with lidocaine for one hour.

Amino Acid Metabolism

Table 1 shows the changes in the medium concentration of some amino acids that are relevant for liver function. A decrease in glutamine concentration was associated with an increased glutamate concentration. Liver metabolism of aromatic amino acids (AAA) was reflected by a decrease in the concentrations of phenylalanine, tyrosine, and tryptophan. Decreased arginine concentrations and synthesis of ornithine are indicative for arginase activity. A decrease in alanine concentration, a precursor of liver gluconeogenesis, was observed.

In addition to table 1, also other amino acids concentrations decreased significantly like, asparagine, glycine, histidine, valine, methionine, isoleucine, leucine, and lysine. Total amino acid metabolism remained stable over a period of three days.

Lactate/Pyruvate Ratio

The lactate/pyruvate ratio is an index for the functional state of cellular oxidation and aerobic metabolism. Table 1 shows a drop in the lactate/pyruvate ratio, which was solely due to a decline in the lactate concentration. The lactate/ pyruvate ratio of 5 to 7 reflected a stable oxygenation status of the culture system over a period of three days.

Enzyme Leakage

To assess the hepatocyte viability, the appearance of enzyme activity, namely LDH, GOT, and GPT, was determined in the culture medium. LDH release was only significant on day one (Table 1). GOT liberation was significant over the three day period with a downward trend in the average GOT concentration. Low but significant quantities of GPT were released on day 1 and 2.

Glucose

Glucose levels did not change on the first day of culture (Table 1). A significant decrease in the glucose concentration was observed on days 2 and 3.

pH

The pH in the studied bioreactor was kept constant (Table 1) with the help of an integrated oxygenator which ensures stable $CO_2$ partial pressures (32.6±0.4 mm Hg, n=8) in the sodium bicarbonate buffered medium.

Protein Secretion

Cultured hepatocytes secrete proteins into their culture medium. A two-dimensional crossed immunoelectrophoresis was performed using an antiserum against pig serum to visualize the different amounts and types of proteins secreted by the hepatocytes cultured in the bioreactor after a 24 hour incubation with supplemented Williams' E medium without FCS. The results are shown in FIG. 6. Each peak represents a different protein. The area under each peak is an indication for the amount of protein secreted. In culture medium from control bioreactors without cells no pig serum proteins were detected (results not shown).

Microscopic Examination

Figure 14:
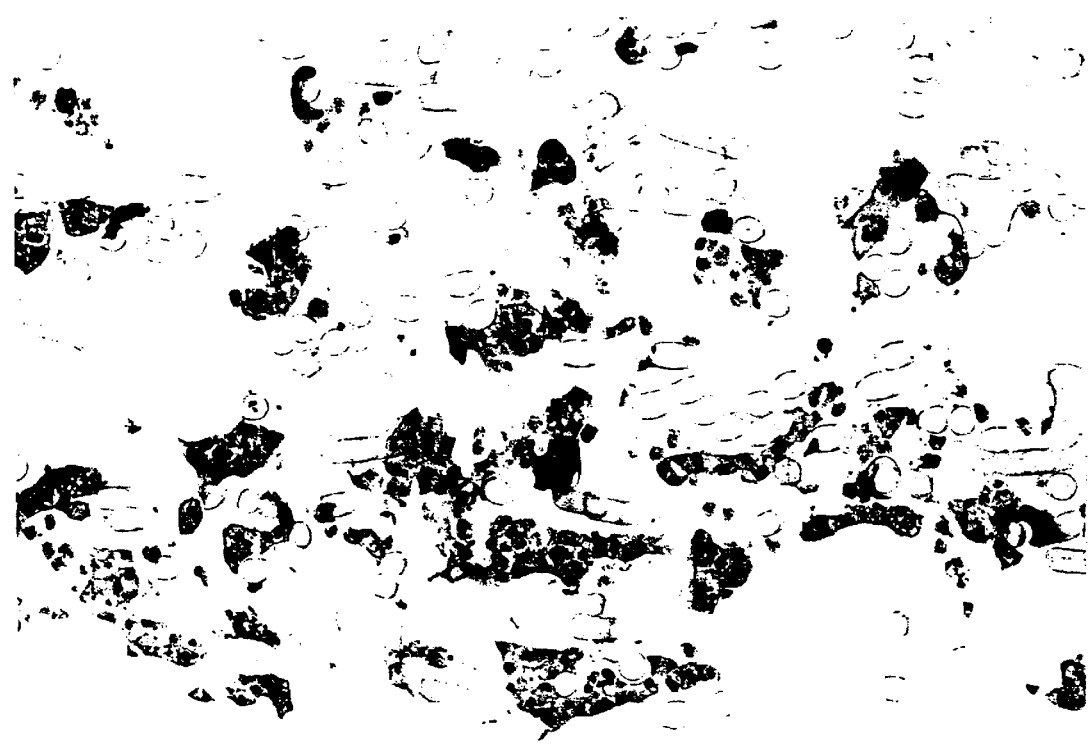
FIG. 14 shows a scanning electron micrograph of isolated porcine hepatocytes cultured for five days in the 3D-matrix of the bioreactor device at $20 \times 10^6$ viable cells/ml.

The hepatocytes from the injected single cell suspension reorganized into small irregular shaped aggregates with extensive cell-cell contact (FIG. 14) The aggregates from this five day old culture were immobilized on and entrapped within the polyester fiber framework. Despite high density culturing there is sufficient room between the aggregates for unhindered perfusion of medium to and from the hepatocytes. As the 3D-matrix is relatively empty it has the potential to culture hepatocytes at even higher densities than the present $20 \times 10^6$ viable cells/ml. Since the aggregates are so small (one diameter never being larger than 5 cells, mostly 2–3 cells), the hepatocytes function in direct medium contact. Medium flow through this hepatocyte immobilization compartment approximates the in vivo situation where every hepatocyte operates under perfusion conditions and close blood contact.

Examination of 3D-matrix samples taken near the inlet and outlet port and in the middle of the nonwoven fabric revealed that the hepatocytes are evenly distributed in the bioreactor device.

Cell counts in twelve microscopic preparations of the 3D-matrix (dimensions: length 10 mm, width 0.5 mm, thickness 8 $\mu$m) of one bioreactor resulted in an average number of 1379±135 (mean±sd) hepatocytes/preparation. One can calculate that if each of the $220 \times 10^6$ seeded viable hepatocytes would immobilize within the nonwoven fabric, every preparation should contain about 1400 viable cells. So, on average 98.5% of the hepatocytes were immobilized in this experiment.

Figure 15:
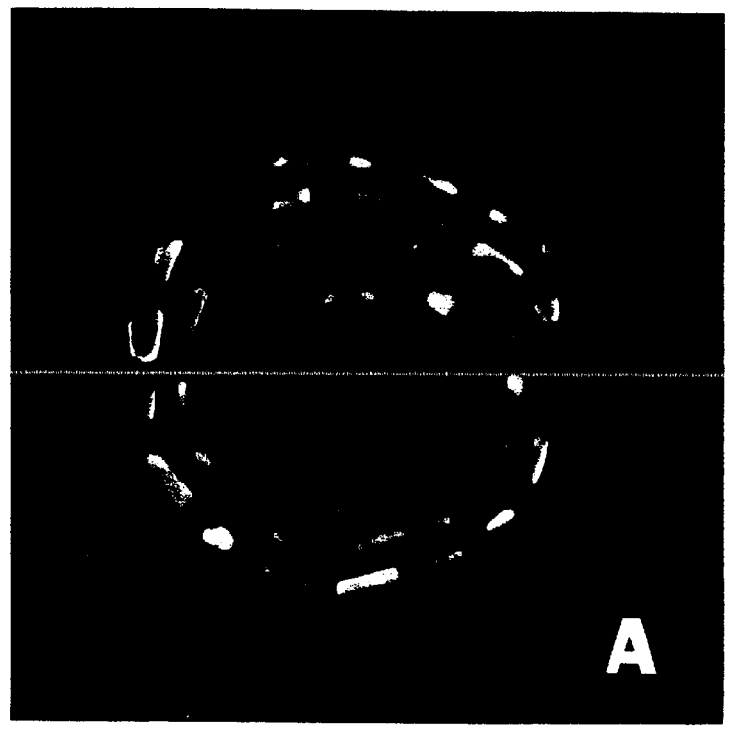
FIGS. 15A and 15B show transactional flow sensitive MRI's of a small (FIG. 15A) internal diameter (1.32 cm) and a scaled-up bioreactor (FIG. 15B) internal diameter (2.2 cm).
Figure 15:
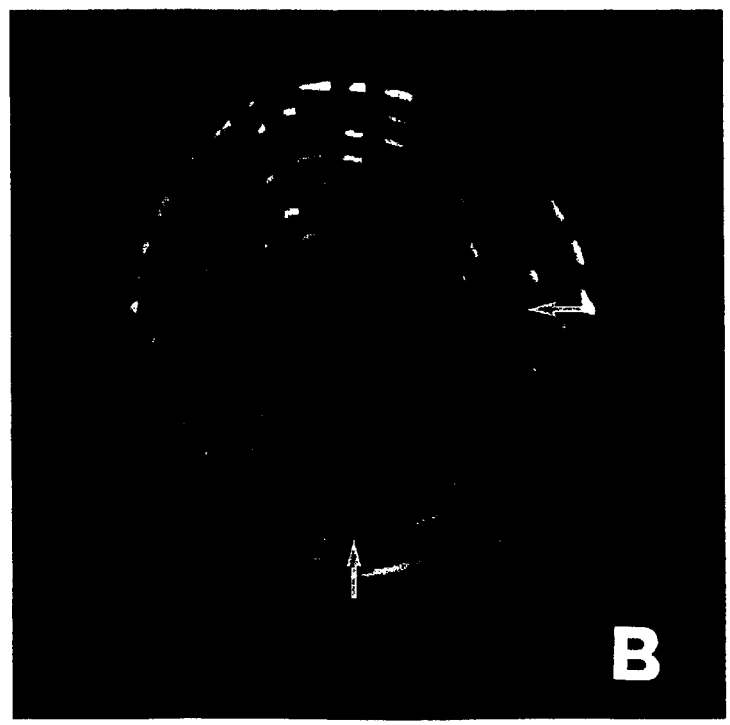

FIG. 15 presents a scanning electron micrograph of isolated hepatocytes after five days in culture in the 3D-matrix of the bioreactor. As observed by light microscopy, the hepatocytes from this five day old culture maintain their aggregate configuration and remain immobilized on the polyester fibers. Extensive cell-cell contact between the spherical hepatocytes can be observed.

Magnetic Resonance Imaging (MRI)

FIGS. 15A and 15B display the flow distribution in a cross-section of a small (A) and a scaled-up bioreactor (B). The fluid velocity was detected only in the axial direction and ranged from zero (black) to around 2 cm/s (white). When compared with FIG. 1 several components of the bioreactor can be identified such as, the nonwoven polyester fabric, the oxygenation hollow-fiber membranes, the flow channels, and the acrylic core. The black representation of the nonwoven polyester fabric indicates only that medium flow within the 3D-matrix was not in the axial direction. The perfusion of the fabric in other directions was not investigated. The homogenous distribution of the gray spots demonstrate that all flow channels in both devices were perfused. The shades of gray indicate that the fluid velocity could differ per flow channel (ranging from 0.5 to 2 cm/s, but mostly around 1.5 cm/s). The arrows in FIG. 2B show spots of decreased signal intensity as a result of entrapped air bubbles. Spin echo images (not shown) revealed that the size of the air bubbles was much smaller than the resulting distortion. The spectrometer only allowed a horizontal orientation of the bioreactor. Normally, the device is positioned vertically, which facilitates the removal of air bubbles.

FIGS. 15A and 15B show transaxial flow sensitive MRI's of a small (FIG. 15A, internal diameter 1.32 cm) and a scaled-up bioreactor (FIG. 15B, internal diameter 2.2 cm). The fluid velocity ranged from zero (black) to around 2 cm/s (white). When compared with FIG. 1 several components of the bioreactor can be identified such as, the nonwoven polyester fabric, the oxygenation hollow-fiber membranes, the flow channels, and the acrylic core. The images of both devices show that all flow channels were perfused. Differences in the fluid velocity of the flow channels can be observed. The arrows in FIG. 15B indicate spots of decreased signal intensity as a result of entrapped air bubbles.

Alpha-GST determination

As expected, the rat alpha-GST concentration increased during BAL-treatment. Remarkably, the pig alpha-GST concentration remained constant, indicating that the viability of the porcine hepatocytes in the bioreactor of the invention was not affected by the toxic rat plasma.

Discussion

In the prior art, hepatocytes have been cultured in the intraluminal and extra fiber space of hollow-fiber units. The popularity of this concept of cell culturing can be easily understood as it is the simplest way of producing a BAL. These systems however do not meet the essential conditions for optimal mass transfer to and from the hepatocytes as present in the intact liver. As a consequence, hepatocyte metabolic activity is impaired for the following reasons:

Clinical treatment of hepatic failure requires large scale, high density hepatocyte culture. In many bioreactors this gives rise to the formation of non-physiological hepatocyte pellets. Hepatocytes in the center of these large aggregates show poor metabolic activity and even possible necrosis due to high gradients as a result of hindered mass transfer of nutrients and oxygen to and carbon dioxide, toxins and cell products from these cells This is in contrast to the in vivo liver where every hepatocyte is in close contact with the blood. Besides, in most bioreactors substrate exchange depends on diffusion which further limits mass transfer compared to the in vivo situation where hepatocytes function under perfusion conditions with corresponding low gradients.

The novel bioreactor of the invention, when used as a BAL addresses the above mentioned requirements for physiological mass transfer. This resulted in a system with the following features:

1. Three-Dimensional Nonwoven Polyester Fabric

Microscopic examination showed that the polyester fibers of the nonwoven fabric provide a framework for high density hepatocyte immobilization ($20 \times 10^6$ cell/ml) and reorganization into small aggregates (one diameter never being larger than 5 cells, mostly 2–3 cells) with room between the aggregates. This allows every cell to operate under in vivo like perfusion conditions and direct medium contact, thereby more closely mimicking physiological gradients. Research on porcine hepatocyte aggregates revealed that such structures maintain many of the cyto-architecture characteristics found in vivo, they survive longer, and show maintained and/or enhanced functional activity compared to monolayer culture. Similar results have been found for our novel bioreactor device which is based on such porcine hepatocyte aggregates. Microscopic evaluation showed extensive contact between spherical shaped hepatocytes as observed in vivo. Liver specific functions were maintained over a period of three days and the urea synthesizing capacity was doubled compared to monolayer culture, in accordance with Lazar et al.

2. No Extracellular Matrix Materials

In a previous study (te Velde AA, Ladiges NCJJ, Flendrig LM, Chamuleau RAFM, J Hepatology 1995; 23:184–192) the functional activity of porcine hepatocytes attached to hydrophilic tissue culture plastic was compared to cells attached to several extracellular matrix constituents: collagen I and IV, laminin, fibronectin, Engelbreth-Holm-Swarm Natrix and in the presence of Matrigel®. With the exception of Matrigel®, neither of the extracellular matrix substrates enhanced pig hepatocyte function compared to tissue culture plastic. Matrigel® has the disadvantage that it is very expensive and moreover, relatively large amounts of murine proteins of tumor origin leak out of the gel and might get into the circulation of the patient. We therefore decided to inject the hepatocyte suspension directly into the dry bioreactor and let the porcine hepatocytes immobilize on the hydrophilic polyester fibers. No prerinsing with medium nor coating with common extracellular matrix materials like Matrigel®, collagen or others was performed, resulting in a safer, cheaper and more convenient device.

3. Rapid Hepatocyte Immobilization

The hepatocytes are allowed to immobilize for two hours. After the immobilization period dead and unattached cells are flushed out of the bioreactor, hence improving the overall viability of the culture system. Theoretically, the system is then ready for use. Light microscopic examination of a five day old bioreactor revealed that 98.5% of the seeded viable hepatocytes were present in the 3D-matrix, indicating high immobilization efficiency and limited cell washout in time. The latter result was confirmed by daily light microscopic examination of medium samples from the closed loop circuit, in which cells or debris were rarely observed.

A short preparation time could be an advantage in clinical application, but additional research needs to demonstrate what the effect this limited recovery time has on hepatocyte function. The rapid immobilization can be explained as follows: after injection of the single-cell hepatocyte suspension, the bioreactor is rotated horizontally along its longitudinal axis for two hours. This continuously changes the sedimentation direction of the suspended cells, which allows the hepatocytes to "shop around" the bioreactor space in search for polyester fibers to attach to. The rotation mode drastically enhances the cell-fiber and cell-cell interactions, thereby accelerating attachment and aggregation of viable hepatocytes. Moreover, the optimal oxygenation status of the system further improves the rate of hepatocyte immobilization.

4. Low Substrate and Metabolite Gradients

On a cellular level low substrate and metabolite gradients in a high density hepatocyte culture can be realized by culturing the hepatocytes as small aggregates inside the nonwoven polyester fabric. This results in hepatocyte culture with sufficient room between the aggregates for unhindered perfusion of all hepatocytes with low medium gradients. When looking at the entire bioreactor, low medium gradients can be obtained by either reducing the perfusion distance between the inlet port and outlet port or by increasing the medium flow rate. Gerlach et al. mentioned hereinabove describe a complicated bioreactor design that realized the former option by culturing the hepatocytes between independently woven hollow-fiber bundles, among one for medium inflow and another for medium outflow. This allows decentralized perfusion of the cells between these capillaries with low gradients. A technically much simpler solution is the latter option by increasing medium flow rate through the bioreactor. This was feasible in our system as the hepatocytes are cultured inside the 3D-matrix and thereby protected by the polyester fiber network. Stepwise increasing the medium flow rate from 5 ml/min. to 15 ml/min. did not reveal any signs of shear stress such as, a decrease in hepatocyte functional activity or an increase in enzyme leakage. Uniform flow and distribution of medium to all parts of the 3D-matrix is ensured by numerous channels, which are evenly distributed throughout the bioreactor space. Moreover, these channels also take care of a homogeneous supply of the injected hepatocyte suspension to the 3D-matrix.

5. Decentralized Oxygenation and Even Oxygenation Hollow-Fiber Distribution

The integrated oxygenator eliminates $O_2$ and $CO_2$ gradients along the perfusion direction of the medium. Furthermore, the spiral wound construction (FIG. 3) creates a homogeneous distribution of the oxygenation hollow-fibers throughout the bioreactor thereby ensuring every hepatocyte of an oxygenation source within its direct surroundings. This results in an optimal oxygenation of the hepatocytes, which was confirmed by a sharp decrease in the lactate/pyruvate ratio (32), and stable pH indicating constant $CO_2$ partial pressures in the sodium bicarbonate buffered medium.

6. Biocompatibility

Biocompatibility has been addressed by constructing the bioreactor of materials that have been FDA approved and withstand the high thermal stress of autoclaving. As far as we know this is the first bioreactor for hepatocyte culture that can be steam-sterilized. This is biologically much safer than the normally used very toxic ethylene oxide sterilization, because ethylene oxide residues leak out of polymers for weeks on end and may cause sensitization and allergic reactions in patients.

7. Easy Scaling Up

The hepatocyte immobilization compartment is composed of many repetitive units. Each unit is fully capable of supporting hepatocyte function and incorporates an oxygenation hollow-fiber, a channel for medium perfusion, and three-dimensional carrier material. Scaling up to the liver mass needed for clinical application simply involves increasing the number of units, thus increasing the number of windings of the hollow-fiber/3D-matrix composite until the required immobilization capacity has been obtained. The use of standard dialysis housings and potting techniques ensure easy manufacturing of a wide range of bioreactor sizes.

Such scaling-up will not influence the plasma distribution in the bioreactor. This was confirmed by flow sensitive MRI, which showed perfusion of all flow channels in a small and a scaled-up bioreactor. The fluid velocity could differ per flow channel, which is a result of the fact that the bioreactors were hand-made. Industrial production techniques are currently being evaluated to solve this.

Also, with the alpha-GST assay mentioned above, for the very first time it is now possible to simultaneously monitor the condition of the liver of the patient and the hepatocytes in the bioreactor. As pig livers are thought to be the hepatocyte source of choice for the years to come this test could be an interesting candidate for monitoring hepatocellular damage during BAL treatment.

A bio-artificial liver support system for the treatment of fulminant hepatic failure and as a bridge to liver transplantation requires large amounts of viable and actively functioning hepatocytes. Pig hepatocytes are considered to be the best alternative, as human hepatocytes are scarcely available and transformed cells may lack critical hepatocyte functions. Pig livers can be obtained from laboratory animals or from the slaughter house, and pig hepatocytes can be easily isolated in large quantities with a simple two-step collagenase perfusion technique.

For clinical application of a bio-artificial liver no long-term cultured hepatocytes are advisable, as the metabolic functions of cultured primary hepatocytes decline with time. Therefore, we monitored the culture system only over the first four days after isolation when liver specific functions are highest. The diversity in liver functions doesn't allow a single test to be an indication for hepatocyte functional capacity. For this reason, a battery of tests was carried out to assess the performance of the culture system. The galactose elimination, urea synthesis and amino acid metabolism remained constant over the investigated period of three days, indicating the ability of the bioreactor system to maintain hepatocyte function.

Lidocaine clearance is an indication for cytochrome P450 activity and is considered the critical function that must be provided by a successful BAL. Lidocaine clearance was maintained over three days, thus demonstrating stable P450 activity by the bioreactor cultured hepatocytes. In one single experiment P450 activity was sustained over 14 days with a gradually decreasing trend in the second week to 70% of the initial activity. To exclude that lidocaine clearance was caused by evaporation, adsorption or unchanged uptake by hepatocytes, biotransformation of lidocaine was investigated by detecting the metabolites MEGX, Xylidine, and GX, known to be synthesized in humans. MEGX is reported to be the main lidocaine metabolite in man and in porcine hepatocytes culture. In contrast, not MEGX but Xylidine was the main lidocaine metabolite on the first two days of culture in this study. Furthermore, porcine hepatocytes did not produce detectable levels of the metabolite GX. In summary, Xylidine and MEGX synthesis confirmed cytochrome P450 activity as demonstrated by the lidocaine clearance. The biotransformation of lidocaine in porcine hepatocytes differed from what has been observed in humans.

The concentration of LDH, GOT, and GPT, used as a marker of cell membrane integrity, decreased rapidly over the investigated period. This drop in enzyme levels probably indicates the recovery of the cultured hepatocytes from the harmful effects of the enzymatic cell isolation technique. The GPT concentrations in our culture system were very low compared to the LDH and GOT levels, which was also observed in the prior art. Therefore, we conclude that the GPT is a poor indicator of porcine hepatocyte membrane integrity and should better be left alone. The most sensitive marker in this study was GOT.

Another important liver function is the protein secretion, which was investigated in the hepatocyte bioreactor on the fourth day of culture. The culture system was able to secrete various proteins as visualized by crossed-over immunoelectrophoresis, each peak representing a different serum protein.

In conclusion, the invention provides a novel bioreactor configuration which ensures maintenance of various liver specific functions at high density hepatocyte culturing. This, together with its ease of handling, manufacturing, and scaling up, makes the system an attractive candidate for short term support of patients in hepatic failure.

TABLE 1

Results of a 14 hour incubation (every day for three days) of $220 \times 10^6$ bioreactor cultured hepatocytes with supplemented Williams 'E medium concerning changes in amino acid concentrations, lactate and pyruvate concentrations and lactate/pyruvate ratios, enzyme leakage, glucose concentrations, and pH

| Evaluation | Unit | t = 0* | day 1 | day 2 | day 3 |
|---|---|---|---|---|---|
| Glutamate** | µM | 402.9 ± 6.6 | 851.3 ± 80.4 | 971.6 ± 62.6 | 1038.2 ± 94.6 |
| Glutamine | µM | 1893.0 ± 47.1 | 881.4 ± 106.6 | 809.3 ± 119.0 | 784.0 ± 124.0 |
| Phenyl-alanine | µM | 155.1 ± 2.2 | 62.1 ± 6.2 | 59.1 ± 6.7 | 68.2 ± 5.03 |
| Tyrosine | µM | 181.7 ± 2.3 | 58.0 ± 12.6 | 51.8 ± 18.2 | 50.6 ± 14.0 |
| Tryptophan | µM | 50.6 ± 0.7 | 20.6 ± 4.1 | 13.5 ± 3.7 | 11.8 ± 1.5 |
| Arginine | µM | 306.9 ± 9.3 | 15.0 ± 2.0 | 15.0 ± 4.4 | 18.4 ± 6.1 |
| Ornithine | µM | 28.2 ± 3.8 | 231.5 ± 24.1 | 229.8 ± 27.7 | 250.4 ± 28.3 |
| Alanine | µM | 1088.4 ± 20.9 | 408.8 ± 89.0 | 457.7 ± 82.0 | 424.6 ± 64.4 |
| Lactate*** | mM | 1.44 ± 0.02 | 0.34 ± 0.07 | 0.26 ± 0.06 | 0.27 ± 0.05 |
| Pyruvate | mM | 0.08 ± 0.004 | 0.05 ± 0.01 | 0.05 ± 0.01 | 0.05 ± 0.004 |
| Lact/Pyr ratio | — | 18.0 ± 0.8 | 6.7 ± 0.8 | 5.4 ± 0.5 | 5.6 ± 0.8 |
| LDH*** | U/L | 14.3 ± 0.9 | 35.2 ± 3.5 | 21.0 ± 2.7 | 14.8 ± 1.3 |
| GOT | U/L | 4.2 ± 0.2 | 169 ± 40 | 120 ± 41.9 | 93 ± 34 |
| GPT | U/L | 0.95 ± 0.2 | 2.1 ± 0.3 | 1.7 ± 0.2 | 1.4 ± 0.2 |
| Glucose*** | mM | 12.0 ± 0.1 | 12.4 ± 0.7 | 10.9 ± 0.4 | 9.6 ± 0.6 |
| pH*** | — | 7.459 ± 0.025 | 7.360 ± 0.020 | 7.394 ± 0.010 | 7.401 ± 0.011 |

*The zero point sample (n = 8) was collected just after an extensive waste wash with supplemented Williams 'E medium.
**mean of 6 experiments in duplicate ± SEM.
***mean of 8 experiments in duplicate ± SEM.

EXAMPLE II

In Vivo Results

The abovementioned BAL was tested with an in vivo rat model.

The used population of rats was divided in three groups.
a. Reference group 1: liver ischemia (LIS) rats given only an infuse.
b. Reference group 2: LIS rats connected to the entire BAL system, but without hepatocytes. This reference is carried out to study the influence of plasmapheresis (possible negative effect) and the large volume of the extra-corporeal circulation (possible positive effect through dilution of toxins) on the survival.
c. LIS rats connected to the BAL with pig hepatocytes.

CONCLUSIONS

The rats were tested for survival. No difference in survival was found between reference groups 1 and 2 (5.9±2.0 hours and 5.5±1.6 hour respectively, n=8). The extra-corporeal circuit therefore has no significant influence on the survival. Compared to the references, LIS rats treated with a BAL system comprising hepatocytes lived twice as long (11.0±2.2 hours, n=5).

This is a remarkable result, not achieved in the prior art, in particular because
a. The model used is very aggressive. Apart from the fact that the rat liver has been completely taken out, toxins leak from the ischemic liver into the rat's circulation, which further detrimentally effects the condition of the tested animal. This is also in accordance with the clinical situation.
b. The rat has not been treated with hepatocytes from its own species, but with pig hepatocytes. This is also in accordance with the clinical situation.

What is claimed is:

1. A bio-artificial organ system comprising a wall surrounding a space, said space comprising:
   (a) a solid support for cell cultivation consisting of a three dimensional matrix in the form of a highly porous sheet or mat, wherein the three dimensional matrix comprises a physiologically acceptable network or fibers or a physiologically acceptable open pore foam structure, wherein the matrix has a porosity of from 40 to about 95% and a pore size of from 10 $\mu$m to 100 $\mu$m, and an overall height of from 50 $\mu$m to about 200 $\mu$m; and
   (b) conduits for supplying gaseous oxygen; wherein said conduits are hollow fibers made of a hydrophobic material and having an outer diameter of 0.1 mm to 1.0 mm, wherein said hollow fibers are evenly distributed through the three dimensional matrix and are arranged in parallel running from one end of the matrix to the other end of the matrix, wherein the distance between individual hollow fibers is between 0.1 mm and 5 mm.

2. The bio-artificial organ system according to claim 1 wherein the cells are selected from the group consisting of liver cells, pancreas cells, kidney cells, parathyroid gland cells, and bone marrow cells.

3. The bio-artificial organ system according to claim 1 wherein the cells are selected from the group consisting of hum an cells and cells derived from non-human animals which are biologically compatible with a human.

4. The bio-artificial organ system according to claim 1 wherein the cells are liver cells selected from the group consisting of primary hepatocytes, immortalized liver cells, liver cell transformants, hepatoma cells, hepatoblasts, and cell lines derived therefrom.

5. The bio-artificial organ system according to claim 4 wherein said liver cells are primary hepatocytes.

6. The bio-artificial organ system according to claim 5 wherein said primary hepatocytes have been subjected to cryopreservation.

7. The bio-artificial organ system according to claim 1 further including at least one gas inlet and at least one gas outlet operably connected to said hollow fibers.

8. The bio-artificial organ system according to claim 1 wherein the hollow fibers are attached to the matrix sheet or mat by weaving said fibers into the matrix sheet or mat, glueing said fibers to said matrix sheet, by sewing said fibers onto the matrix sheet or mat, bonding said fibers to said matrix sheet or mat by means of ultrasound.

9. The bio-artificial organ according to claim 1 wherein said solid support is present in the form of at least one rolled or folded sheet or mat or at least two stacked sheets or mats.

10. A method for maintaining and/or cultivating organ cells comprising introducing said cells into the space of the bio-artificial organ according to claim 7 so that said cells adhere to the solid support, and keeping these cells under physiologically acceptable conditions while supplying gaseous oxygen or an oxygen containing gas through said at least one gas inlet operably connected to the hollow fibers.

11. The method according to claim 10 wherein, after the cells have been introduced into the space of the bio-artificial organ, the cells are immobilized on the solid support located in the bioartificial organ by rotating the bioartificial organ around an internal or an external longitudinal axis for a period of time sufficient to allow the cells to adhere to said solid support.

12. The method according to claim 11 wherein said rotating is around the external longitudinal axis.

13. The method according to claim 10 wherein the organ cells are liver cells selected from the group consisting of primary hepatocytes, immortalized liver cells, liver cell transformants, hepatoma cells, hepatoblasts, and cell lines derived therefrom.

* * * * *